United States Patent

Baumann et al.

[11] Patent Number: 5,750,469
[45] Date of Patent: May 12, 1998

[54] SUBTITUTED LACTIC ACID DERIVATIVES HAVING AN N-ORGANIC RADICAL IN THE β-POSITION

[75] Inventors: Ernst Baumann, Dudenhofen; Joachim Rheinheimer; Uwe Josef Vogelbacher, both of Ludwigshafen; Matthias Gerber; Wilhelm Rademacher, both of Limburgerhof; Helmut Walter, Obrigheim; Karl-Otto Westphalen, Speyer, all of Germany

[73] Assignee: BASF Aktiengesellschaft, Ludwigshafen, Germany

[21] Appl. No.: 605,141

[22] PCT Filed: Sep. 25, 1994

[86] PCT No.: PCT/EP94/02825

§ 371 Date: Mar. 1, 1996

§ 102(e) Date: Mar. 1, 1996

[87] PCT Pub. No.: WO95/07266

PCT Pub. Date: Mar. 16, 1995

[30] Foreign Application Priority Data

Sep. 4, 1993 [DE] Germany ............... 43 29 911.3

[51] Int. Cl.⁶ ............... C07D 239/60; A01N 43/54
[52] U.S. Cl. ............... 504/243; 544/238; 544/295; 544/296; 544/212; 544/209; 544/219; 544/300; 544/301; 544/302; 544/310; 540/598; 540/601; 540/480; 540/481; 504/219; 504/230; 504/236; 504/235; 504/237; 504/238
[58] Field of Search ............... 504/240, 241, 504/242, 243, 219, 235; 544/278, 253, 310, 312, 313, 314, 316, 318, 300, 301; 540/598, 481

[56] References Cited

U.S. PATENT DOCUMENTS

| | | | |
|---|---|---|---|
| 5,270,289 | 12/1993 | Harde et al. | 504/243 |
| 5,326,744 | 7/1994 | Rheinheimer et al. | 504/241 |
| 5,446,013 | 8/1995 | Zurmuehlen et al. | 504/242 |

FOREIGN PATENT DOCUMENTS 347 811  12/1989  European Pat. Off. .

(List continued on next page.)

*Primary Examiner*—John M. Ford
*Attorney, Agent, or Firm*—Keil & Weinkauf

[57] ABSTRACT

Substituted lactic acid derivatives having an N-organic radical in the β-position, of the formula I

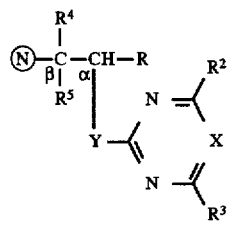

I where substituents R to $R^5$, X and Y have the meanings mentioned in the description and Ⓝ is one of the radicals:

a) $-N_3$, $-NC$, $-NCS$ or $-NCO$ b)

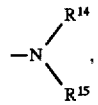

where $R^{14}$ and $R^{15}$ have the meanings described in the description c)

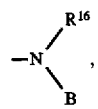

in which
$R^{16}$ is hydrogen, alkyl, haloalkyl, alkenyl, alkynyl, cycloalkyl or unsubstituted or substituted phenyl; and
B is a group

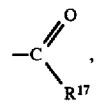

$OR^{19}$ or $-NR^{14}R^{15}$, where $R^{14}$, $R^{15}$, $R^{17}$ and $R^{19}$ have the meanings described in the description, or

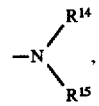

where $R^{14}$ and $R^{15}{}_1$, have the abovementioned meanings; or

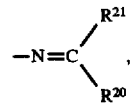

where $R^{20}$ and $R^{21}$, which can be identical or different, are:
hydrogen, alkyl, alkenyl, alkynyl, cycloalkyl or phenyl, where the organic radicals can in each case be substituted; or $R^{20}$ and $R^{21}$ together form an unsubstituted or substituted $C_4$–$C_7$-alkylene chain which is closed to give a ring or together form an unsubstituted or substituted $C_3$–$C_6$-alkylene chain which is closed to give a ring and has a heteroatom selected from the group consisting of oxygen, sulfur and nitrogen are described.

9 Claims, No Drawings

FOREIGN PATENT DOCUMENTS

| | | |
|---|---|---|
| 400 741 | 12/1990 | European Pat. Off. . |
| 409 368 | 1/1991 | European Pat. Off. . |
| 481 512 | 4/1992 | European Pat. Off. . |
| 517 215 | 12/1992 | European Pat. Off. . |
| 541 041 | 5/1993 | European Pat. Off. . |
| 548 710 | 6/1993 | European Pat. Off. . |

SUBSTITUTED LACTIC ACID DERIVATIVES HAVING AN N-ORGANIC RADICAL IN THE β-POSITION

This is a 371 of PCT EP94/02825 filed Sep. 25, 1994.

The present invention relates to substituted lactic acid derivatives having an N-organic radical in the β-position, of the formula I

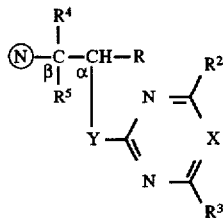

where R is a formyl group, a group $CO_2H$ or a radical which can be hydrolyzed to give COOH and the other substituents have the following meanings:

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is $CR^{13}$, $R^{13}$ being hydrogen or together with $R^3$ forming a 3- or 4-membered alkylene or alkenylene chain in which one methylene group in each case is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, or $R^3$ is linked with $R^{13}$ as indicated above to give a 5- or 6-membered ring;

$R^4$ is in each case unsubstituted or substituted cycloalkyl, cycloalkenyl, it being possible for a $CH_2$ group in the ring to be replaced by an oxygen or sulfur atom, alkyl, alkenyl, alkynyl, phenyl, naphthyl or a five- or six-membered heteroaromatic comprising one to three nitrogen atoms and/or one sulfur or oxygen atom;

or $R^4$ and $R^5$, together with the adjacent carbon atom, form a 3- to 8-membered ring which can contain one oxygen or sulfur atom and can carry one to three of the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^5$ is hydrogen, alkyl, alkenyl, alkynyl, alkylcarbonyl, alkoxycarbonyl, haloalkyl, cycloalkyl, alkoxyalkyl, alkylthioalkyl or unsubstituted or substituted phenyl, or $R^5$ is linked with $R^4$ as indicated above to give a ring;

Y is sulfur, oxygen or a single bond;

Ⓝ is a) a radical —$N_3$, —NC, —NCS or —NCO b) a radical

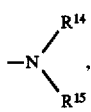

where $R^{14}$ and $R^{15}$ are hydrogen, an aliphatic, cycloaliphatic or aromatic C-organic radical having up to 20 carbon atoms or together form an unsubstituted or substituted $C_4$–$C_7$-alkylene chain which is closed to give a ring, in which a methylene group can be replaced by oxygen, sulfur or nitrogen;

c) a radical

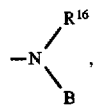

where the radicals have the following meanings:
$R^{16}$ is hydrogen, alkyl, haloalkyl, alkenyl, alkynyl, cycloalkyl or unsubstituted or substituted phenyl;
B is a group

$OR^{19}$ or —$NR^{14}R^{15}$, where $R^{14}$ and $R^{15}$ have the abovementioned meanings and $R^{17}$ or $R^{19}$ is defined as follows:

$R^{17}$ is hydrogen, alkyl, haloalkyl, alkenyl, alkynyl, cycloalkyl, phenyl or substituted phenyl;
a radical $OR^{18}$ in which $R^{18}$ is
hydrogen, alkyl, haloalkyl, alkenyl, alkynyl, cycloalkyl, phenyl or substituted phenyl;
a radical

where $R^{14}$ and $R^{15}$, have the abovementioned meanings;

$R^{19}$ is hydrogen, alkyl, haloalkyl, alkenyl, alkynyl, cycloalkyl, phenyl or substituted phenyl;

d) a radical

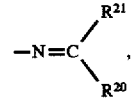

where $R^{20}$ and $R^{21}$, which can be identical or different, are:
hydrogen, alkyl, alkenyl, alkynyl, cycloalkyl or phenyl, where the organic radicals can in each case be substituted;
or $R^{20}$ and $R^{21}$ together form an unsubstituted or substituted $C_4$–$C_7$-alkylene chain which is closed to give a ring or together form an unsubstituted or substituted $C_3$–$C_6$-alkylene chain which is closed to give a ring and has a heteroatom selected from the group consisting of oxygen, sulfur and nitrogen.

In the literature, e.g. EP-A 347 811, EP-A 400 741, EP-A 409 368, EP-A 481 512, EP-A 517 215, EP-A 541 041, JP 043 34372-A and EP-A 548 710, similar compounds are described as herbicidally active. The biological action and selectivity of these compounds, however, is not always satisfactory.

It is an object of the present invention to provide compounds having improved selectivity toward crop plants and/or better herbicidal or bioregulatory action.

We have found that this object is achieved by the lactic acid derivatives I defined at the outset, which have excellent herbicidal and plant growth-regulating properties. We have moreover found that the lactic acid derivatives I have a good antagonistic action against herbicides of the cyclohexenone type XIII.

The invention therefore also relates to herbicidal compositions, comprising a lactic acid derivative of the formula I and at least one herbicidal active compound from the group of cyclohexenone derivatives of the general formula XIII

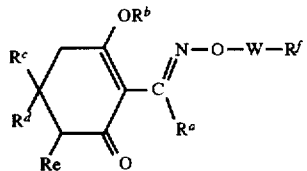

where the substituents have the following meanings:

$R^a$ is a $C_1$–$C_6$-alkyl group;

$R^b$ is hydrogen, the equivalent of an agriculturally utilizable cation, a $C_2$–$C_8$-alkylcarbonyl group, a $C_1$–$C_{10}$-alkylsulfonyl group, a $C_1$–$C_{10}$-alkylphosphonyl group or the benzoyl, benzenesulfonyl or benzenephosphonyl group, where the three last-mentioned groups can additionally each carry 1 to 5 halogen atoms;

$R^c$ is hydrogen or a C-organic radical;

$R^d$ is hydrogen, the hydroxyl group or, if $R^c$ is a $C_1$–$C_6$-alkyl group, is a $C_1$–$C_6$-alkyl group;

$R^e$ is hydrogen, halogen, the cyano group, a $C_1$–$C_4$-alkoxycarbonyl group or a $C_1$–$C_4$-alkylketoxime group;

W is a $C_1$–$C_6$-alkylene, $C_3$–$C_6$-alkenylene or $C_3$–$C_6$-alkynylene chain which each can additionally carry one to three radicals selected from a group consisting of one to three $C_1$–$C_3$-alkyl substituents, one to three halogen atoms and one methylene substituent;

a $C_3$–$C_6$-alkylene or $C_4$–$C_6$-alkenylene chain which both additionally can carry one to three $C_1$–$C_3$-alkyl radicals, where in each case one methylene group of the chains can be substituted by an oxygen or sulfur atom, a sulfoxide or sulfone group or a group —N($R^i$)—, where $R^i$ is hydrogen, $C_1$–$C_4$-alkyl, $C_3$–$C_6$-alkenyl or $C_3$–$C_6$-alkynyl;

$R^f$ is hydrogen; an unsubstituted or substituted vinyl or ethynyl group, unsubstituted or substituted phenyl or an unsubstituted or substituted 5- or 6-membered heteroaromatic radical.

It was furthermore surprisingly found that the compounds I have a good pharmacological activity, in particular in the cardiovascular field.

The preparation of the compounds according to the invention is possible in various ways which are described in the following text.

Preparation route A

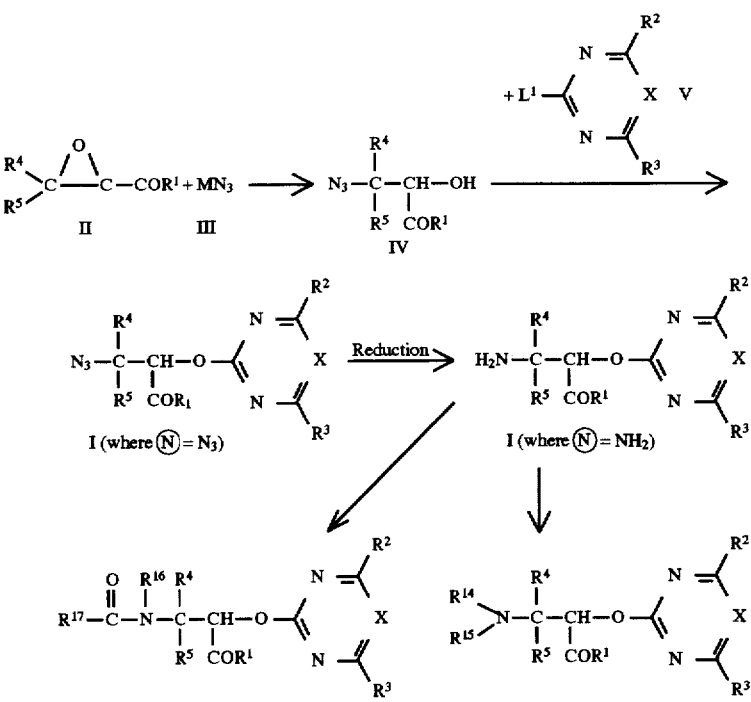

By reaction of epoxides of the general formula II, which are known or can be prepared in accordance with general technical knowledge, starting from known precursors (cf. for example J. March, Advanced Organic Chemistry, 2nd Edition, 1983, pp. 750 and 862), with a suitable azide $MN_3$ III, in which M is hydrogen, an alkali metal cation (e.g. Na, K), the equivalent of an alkaline earth metal cation (e.g. Mg) or a silyl radical $SiR_3$, where the radicals R can be identical or different and are, for example, lower alkyl or phenyl, the azidoalcohols of the general formula IV are obtained in which $R^1$, $R^4$ and $R^5$ have the meanings mentioned in claim 1.

The reaction can also be carried out in the presence of a diluent. For this purpose, all solvents which are inert to the reagents used can be used.

Examples of solvents or diluents of this type are water, aliphatic, alicyclic and aromatic hydrocarbons which in each case can be unchlorinated or chlorinated, for example hexane, cyclohexane, petroleum ether, ligroin, benzene, toluene, xylene, methylene chloride, chloroform, carbon tetrachloride, ethylene chloride and trichloroethylene, ethers, for example diisopropyl ether, dibutyl ether, propylene oxide, dioxane and tetrahydrofuran, ketones, for example acetone, methyl ethyl ketone, methyl isopropyl ketone and methyl isobutyl ketone, nitriles, for example acetonitrile and propionitrile, alcohols, for example methanol, ethanol, isopropanol, butanol and ethylene glycol, esters, for example ethyl acetate and amyl acetate, acid amides, for example dimethylformamide and dimethylacetamide, sulfoxides and sulfones, for example dimethyl sulfoxide and sulfolane, and bases, for example pyridine.

The reaction is in this case preferably carried out in a temperature range from 0° C. to the boiling point of the solvent or solvent mixture.

The presence of a reaction catalyst can be advantageous. Possible catalysts in this case are organic acids and inorganic acids and also Lewis acids. Examples of these, inter alia, are sulfuric acid, hydrochloric acid, trifluoroacetic acid, boron trifluoride etherate, titanium(IV) halides and trimethylsilyl triflate.

The compounds according to the invention in which Y is oxygen and Ⓝ is $N_3$ and the remaining substituents have the meanings mentioned under the general formula I can be prepared, for example, by reacting the azidoalcohols of the general formula IV with compounds of the general formula V in which $L^1$ is a customary nucleofugic leaving group such as halogen, e.g. chlorine or bromine, alkylsulfonyl, for example $C_1$–$C_4$-alkylsulfonyl such as methylsulfonyl or arylsulfonyl, e.g. phenylsulfonyl.

The reaction preferably takes place in one of the abovementioned diluents with addition of a suitable base, i.e. a base which is able to deprotonate the compound IV, in a temperature range from room temperature up to the boiling point of the solvent.

The base used can be an alkali metal or alkaline earth metal hydride such as sodium hydride, potassium hydride or calcium hydride, a carbonate, e.g. alkali metal carbonate such as sodium or potassium carbonate, an alkali metal hydroxide such as sodium or potassium hydroxide, an organometallic compound such as butyllithium or an alkali metal amide such as lithium diisopropylamide.

The azido function in the compounds of the general formula I thus obtained can be reduced to the amino function by customary methods, for example using hydrogen in the presence of a noble metal catalyst. The compounds of the general formula I thus obtained, in which Ⓝ is —$NH_2$ and Y is oxygen, can be reacted by known methods, for example by reactions with an acid chloride $R^{17}COCl$ or acid anhydride $(R^{17}CO)_2O$ or a compound $R^{14}L^2$ or $R^{15}L^2$, where $L^2$ is a nucleofugic leaving group, as mentioned above, to give further compounds of the general formula I.

Preparation route B

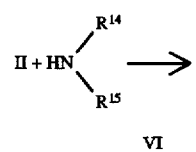

VI

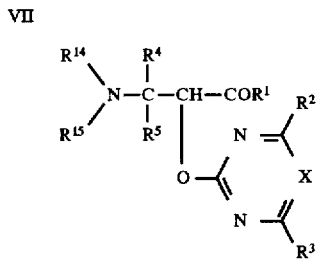

The opening of epoxides II using amines of the general formula VI to give compounds of the general formula VII, in which the substituents have the meanings mentioned in claim 1, is known (e.g. Zymalkowski, Arch. Pharmazie (Weinheim) 312 (1979) 138). The compounds of the general formula I according to the invention, in which Y is oxygen, Ⓝ is —$NR^{14}R^{15}$ and the other substituents have the meanings mentioned under the general formula I, can be prepared, for example, by reacting the compounds of the general formula VII with compounds of the general formula V as described under preparation route A.

Preparation route C

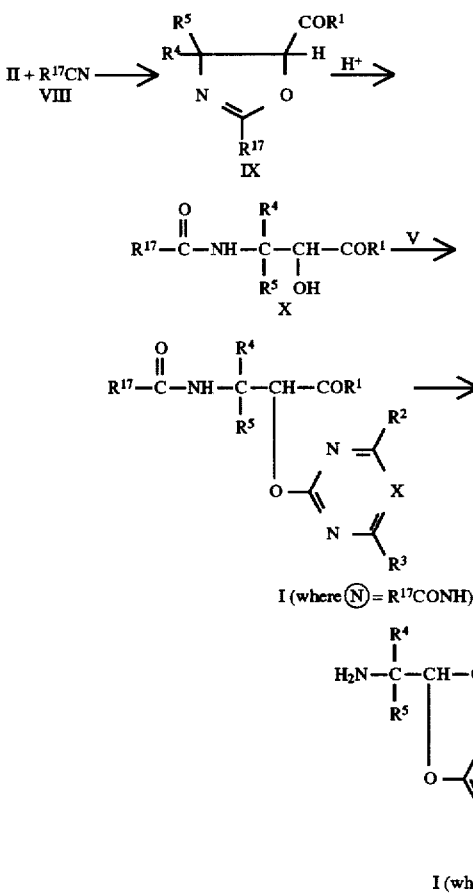

The reaction of epoxides of the general formula II with nitriles of the general formula VIII in the presence of the diluents and/or catalysts mentioned under preparation route A leads to oxazolines of the general formula IX in which the substituents have the meanings mentioned in claim 1. These are then opened in one of the abovementioned inert solvents with addition of a catalytic amount of a dilute mineral acid to give compounds of the general formula X.

The compounds of the general formula I according to the invention, in which Y is oxygen, ⓝ is —NHCOR$^{17}$ and the other substituents have the meanings mentioned under the general formula I, can now be prepared, for example, by reacting the compounds of the general formula X with compounds of the general formula V, as described under preparation route A.

The compounds thus obtained can be reacted further by treatment with aqueous acid or base to give compounds of the general formula I in which Y is oxygen, ⓝ is —NH$_2$ and the other substituents have the meanings mentioned under the general formula I, where these in turn are used as starting materials for further compounds of the formula I as described in preparation route A.

Preparation route D

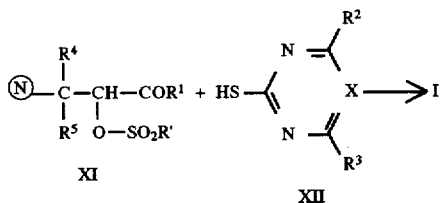

The compounds according to the invention in which Y is sulfur and the remaining substituents have the meanings indicated under formula I can be prepared, for example, by reacting lactic acid derivatives of the general formula XI which are obtainable in a known manner, for example, from compounds of the general formula IV, VII or X and in which R' is lower alkyl or haloalkyl, e.g. having up to 6 carbon atoms or unsubstituted or substituted phenyl and the other substituents have the meanings indicated above, with compounds of the general formula XII which are known or which can be prepared with general technical knowledge, starting from known precursors, and in which $R^2$, $R^3$ and X have the meanings indicated under the general formula I.

The reaction preferably takes place in one of the abovementioned inert diluents with addition of a suitable base, i.e. a base which is able to deprotonate the intermediate XII, in a temperature range from room temperature up to the boiling point of the solvent.

In addition to the abovementioned bases, the base used can also be organic bases such as triethylamine, pyridine, imidazole or diazabicycloundecane.

Preparation route E

Compounds of the formula I can also be prepared by starting from the corresponding carboxylic acids, i.e. compounds of the formula I in which $R^1$ is hydroxyl, and converting these first in a customary manner into an activated form such as a halide, an anhydride or imidazolide and then reacting this with an appropriate hydroxyl compound HOR$^9$. This reaction can be carried out in the customary solvents and is advantageously performed in the presence of a base, those mentioned above being suitable. These two steps can be simplified, for example, by allowing the carboxylic acid to act on the hydroxyl compound in the presence of a dehydrating agent such as a carbodiimide.

Preparation route F

Additionally, compounds of the formula I can also be prepared by starting from the salts of the corresponding carboxylic acids, i.e. from compounds of the formula I in which $R^1$ is OM, where M can be an alkali metal cation or the equivalent of an alkaline earth metal cation. These salts can be reacted with many compounds of the formula $R^1$—A, A being a customary nucleofugic leaving group, for example halogen such as chlorine, bromine, iodine or aryl- or alkylsulfonyl which is unsubstituted or substituted by halogen, alkyl or haloalkyl, for example toluenesulfonyl and methylsulfonyl or another equivalent leaving group. Compounds of the formula $R^1$—A having a reactive substituent A are known or easily accessible in accordance with general technical knowledge. This reaction can be carried out in the customary solvents and is advantageously performed in the presence of a base, those mentioned above being suitable.

With respect to biological action, lactic acid derivatives of the formula I are preferred in which the substituents have the following meanings:

$R^1$ is
a) hydrogen;
b) a succinylimidoxy group;
c) a 5-membered heteroaromatic linked via a nitrogen atom and containing one to three nitrogen atoms, such as pyrrolyl, pyrazolyl, imidazolyl and triazolyl, which can carry one or two halogen atoms, in particular fluorine or chlorine and/or one or two of the following radicals:

$C_1$–$C_4$-alkyl such as methyl, ethyl, 1-propyl, 2-propyl, 2-methyl-2-propyl, 2-methyl-1-propyl, 1-butyl, 2-butyl;

$C_1$–$C_4$-haloalkyl, in particular $C_1$–$C_2$-haloalkyl such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_1$–$C_4$-haloalkoxy, in particular $C_1$–$C_2$-haloalkoxy such as difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy;

$C_1$–$C_4$-alkoxy such as methoxy, ethoxy, propoxy, 1-methylethoxy, butoxy, 1-methylpropoxy, 2-methylpropoxy, 1,1-dimethylethoxy, in particular methoxy, ethoxy, 1-methylethoxy;

$C_1$–$C_4$-alkylthio such as methylthio, ethylthio, propylthio, 1-methylethylthio, butylthio, 1-methylpropylthio, 2-methylpropylthio, 1,1-dimethylethylthio, in particular methylthio and ethylthio;

d) $R^1$ is further a radical —(O)$_m$—NR$^6$R$^7$ in which m is 0 or 1 and $R^6$ and $R^7$, which can be identical or different, have the following meanings:
hydrogen;
$C_1$–$C_8$-alkyl, in particular $C_1$–$C_4$-alkyl as mentioned above;
$C_3$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-ethyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-triethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl;

$C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably 2-propynyl, 2-butynyl, 1-methyl-2-propynyl and 1-methyl-2-butynyl, in particular 2-propynyl;

$C_3$–$C_8$-cycloalkyl, such as cyclopropyl, cyclobutyl, cyclopentyl, cyclohexyl, cycloheptyl and cyclooctyl, where these alkyl, cycloalkyl, alkenyl and alkynyl groups can each carry one to five, in particular one to three, halogen atoms, preferably fluorine or chlorine and/or one or two of the following groups:

$C_1$–$C_4$-alkyl, $C_1$–$C_4$-alkoxy, $C_1$–$C_4$-alkylthio, $C_1$–$C_4$-haloalkoxy and $C_3$–$C_8$-cycloalkyl, in each case as mentioned above, $C_3$–$C_6$-alkenyloxy, $C_3$–$C_6$-alkenylthio, $C_3$–$C_6$-alkynyloxy, $C_3$–$C_6$-alkynylthio, where the alkenyl and alkynyl constituents present in these radicals preferably correspond to the abovementioned meanings;

$C_1$–$C_4$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl;

$C_1$–$C_4$-alkoxycarbonyl such as methoxycarbonyl, ethoxycarbonyl, propyloxycarbonyl, 1-methylethoxycarbonyl, butyloxycarbonyl, 1-methylpropyloxycarbonyl, 2-methylpropyloxycarbonyl, 1,1-dimethylethoxycarbonyl;

$C_3$–$C_6$-alkenylcarbonyl, $C_3$–$C_6$-alkynylcarbonyl, $C_3$–$C_6$-alkenyloxycarbonyl and $C_3$–$C_6$-alkynyloxycarbonyl, where the alkenyl and alkynyl radicals are preferably defined as listed in detail above;

phenyl, if desired mono- or polysubstituted, e.g. mono- to trisubstituted, by halogen, e.g. F, Cl, Br, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, such as 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoxyphenyl, 2-methylthiophenyl, 2,4-dichlorophenyl, 2-methoxy-3-methylphenyl, 2,4-dimethoxyphenyl, 2-nitro-5-cyanophenyl, 2,6-difluorophenyl;

di-$C_1$–$C_4$-alkylamino such as, in particular, dimethylamino, dipropylamino, N-propyl-N-methylamino, N-propyl-N-ethylamino, diisopropylamino, N-isopropyl-N-methylamino, N-isopropyl-N-ethylamino, N-isopropyl-N-propylamino;

$R^6$ and $R^7$ are further phenyl which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, as mentioned in detail above;

or $R^6$ and $R^7$ together form an unsubstituted or substituted $C_4$–$C_7$-alkylene chain which is closed to give a ring and which can contain a heteroatom selected from the group consisting of oxygen, sulfur and nitrogen, such as —$(CH_2)_4$—, —$(CH_2)_5$—, —$(CH_2)_6$—, —$(CH_2)_7$—, —$(CH_2)_2$—O—$(CH_2)_2$—, —$CH_2$—S—$(CH_2)_3$—, —$(CH_2)_2$—O—$(CH_2)_3$—, —NH—$(CH_2)3$—, —$CH_2$—NH—$(CH_2)_2$—, —$CH_2$—CH=$CH_2$—, —CH=CH—$(CH_2)_3$—, suitable substituents being, in particular, $C_1$–$C_4$-alkyl radicals, e.g. methyl;

e) $R^1$ is further a group

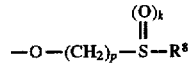

where k can assume the values 0, 1 or 2, p can assume the values 1, 2, 3 and 4 and $R^8$ is $C_1$–$C_4$-alkyl, $C_1$–$C_4$-haloalkyl, $C_3$–$C_6$-alkenyl, $C_3$–$C_6$-alkynyl or unsubstituted or substituted phenyl, such as mentioned in particular for $R^6$ and $R^7$;

f) $R^1$ is further a radical $OR^9$, in which $R^9$ is:
 i) hydrogen, the cation of an alkali metal or the cation of an alkaline earth metal, such as lithium, sodium, potassium, calcium, magnesium and barium, or an environmentally tolerable organic ammonium ion such as tert-$C_1$–$C_4$-alkylammonium or ammonium[$NH_4^+$];
 ii) $C_3$–$C_8$-cycloalkyl as mentioned above, which can carry, for example, one to three $C_1$–$C_4$-alkyl groups;
 iii) $C_1$–$C_8$-alkyl such as, in particular, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, which can carry one to five halogen atoms, in particular fluorine or chlorine and/or one of the following radicals:

$C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$- alkoxycarbonyl, phenyl, phenyl or phenoxy which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, such as mentioned above in particular;

iv) a $C_1$–$C_8$-alkyl group as mentioned above, which can carry one to five, preferably one to three, halogen atoms, in particular fluorine and/or chlorine, and carries one of the following radicals: a 5-membered heteroaromatic, containing one to three nitrogen atoms or a 5-membered heteroaromatic, containing a nitrogen atom and an oxygen or sulfur atom, such as pyrazolyl, imidazolyl, benzimidazolyl, triazolyl, benzotriazolyl, isoxazolyl, oxazolyl, thiazolyl, bonded via a C atom or, if possible, N atom, where the heteroaromatic can carry one to four halogen atoms and/or one or two of the following radicals: nitro, cyano, $C_1$–$C_4$-alkyl, $C_1$–$C_4$-haloalkyl, $C_1$–$C_4$-alkoxy, phenyl, $C_1$–$C_4$-haloalkoxy and/ or $C_1$–$C_4$-alkylthio. The following may be mentioned in particular: 1-pyrazolyl, 3-methyl-1-pyrazolyl, 4-methyl-1-pyrazolyl, 3,5-di-methyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropylisoxazol-5-yl, 3-methylisoxazol-5-yl, oxazol-2-yl, thiazol-2-yl, imidazol-2-yl, 3-ethylisoxazol-5-yl, 3-phenylisoxazol-5-yl, 3-tert-butylisoxazol-5-yl;

v) a $C_2$–$C_6$-alkyl group which in the 2-position carries one of the following radicals: $C_1$–$C_4$-alkoxyimino, $C_3$–$C_6$-alkynyloxyimino, $C_3$–$C_6$-haloalkenyloxyimino or benzyloxyimino;

vi) a $C_3$–$C_6$-alkenyl or a $C_3$–$C_6$-alkynyl group such as mentioned above in particular, where these groups for their part can carry one to five halogen atoms;

vii) $R^9$ is further a phenyl radical which can carry one to five halogen atoms and/or one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, such as mentioned above in particular;

viii) a 5-membered heteroaromatic linked via a nitrogen atom, containing one to three nitrogen atoms such as pyrazolyl, imidazolyl, benzimidazolyl, triazolyl, benzotriazolyl, preferably bonded via the 1-position, where the heteroaromatic can carry one or two halogen atoms and/or one or two of the following radicals:

$C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. The following may be mentioned in particular: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3,4-dichloroimidazol-1-yl;

ix) $R^9$ is further a group

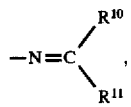

where $R^{10}$ and $R^{11}$, which can be identical or different, are: $C_1$–$C_8$-alkyl, $C_3$–$C_6$-alkenyl, $C_3$–$C_6$-alkynyl, $C_3$–$C_8$-cycloalkyl, where these radicals can carry a $C_1$–$C_4$-alkoxy, $C_1$–$C_4$-alkylthio and/or an unsubstituted or substituted phenyl radical, such as mentioned above in particular;

phenyl, which can be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, where these radicals in particular correspond to those mentioned above for $R^1$;

or $R^{10}$ and $R^{11}$ together form a $C_3$–$C_{12}$-alkylene chain which can carry one to three $C_1$–$C_4$-alkyl groups and can contain a heteroatom from the group consisting of oxygen, sulfur and nitrogen, such as mentioned in particular in the case of $R^6$ and $R^7$.

g) $R^1$ is further a radical —NH—$SO_2$—$R^{12}$, in which $R^{12}$ is:

$C_1$–$C_4$-alkyl, $C_3$–$C_6$-alkenyl, $C_3$–$C_6$-alkynyl, $C_3$–$C_8$-cycloalkyl such as mentioned above in particular for $R^1$, where these radicals can carry a $C_1$–$C_4$-alkoxy, $C_1$–$C_4$-alkylthio and/or a phenyl radical as mentioned above;

phenyl, unsubstituted or substituted, in particular as mentioned above;

$R^2$ is the $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio groups and halogen atoms mentioned in detail in the case of $R^1$, in particular chlorine, methyl, methoxy, ethyl, difluoromethoxy, trifluoromethoxy, particularly preferably methoxy;

X is nitrogen or $CR^{13}$, in which $R^{13}$ is preferably hydrogen or together with $R^3$ forms a 4- to 5-membered alkylene or alkenylene chain in which one methylene group is in each case replaced by oxygen, such as —$CH_2$—$CH_2$—O—, —CH=CH—O—, —$CH_2$—$CH_2$—$CH_2$—O—, —CH=CH—$CH_2$O—, in particular hydrogen and —$CH_2$—$CH_2$—O—;

$R^3$ is the $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio groups and halogen atoms mentioned in the case of $R^1$, in particular chlorine, methyl, methoxy, ethoxy, difluoromethoxy, trifluoromethoxy, particularly preferably methoxy, or is linked with $R^{13}$ as mentioned above to give a 5- or 6-membered ring;

$R^4$ is $C_1$–$C_8$-alkyl as mentioned in detail in the case of $R^1$, which can carry one to five halogen atoms such as fluorine, chlorine, bromine, iodine, in particular fluorine and chlorine and/or one of the following radicals: $C_1$–$C_4$-alkoxy, $C_1$–$C_4$-alkylthio, cyano, hydroxyl, $C_1$–$C_4$-alkylcarbonyl, $C_1$–$C_4$-alkoxycarbonyl, phenyl, phenoxy, phenylcarbonyl as mentioned in general and particular in the case of $R^1$;

$C_1$–$C_8$-alkyl as mentioned above, which can carry one to five halogen atoms as mentioned above, in particular fluorine or chlorine, and carries an unsubstituted or substituted 5-membered heteroaromatic, such as mentioned above for $R^1$;

$C_3$–$C_8$-cycloalkyl or $C_3$–$C_8$-cycloalkenyl, where a methylene group in the saturated or unsaturated ring can be replaced by an oxygen or sulfur atom, such as cyclopropyl, cyclobutyl, cyclopentyl, cyclohexyl, cycloheptyl, cyclooctyl, tetrahydrofuranyl, tetrahydrothienyl, tetrahydropyranyl, tetrahydrothiopyranyl, cyclopropenyl, dihydrofuranyl, dihydrothienyl, dihydropyranyl, dihydrothiopyranyl, where the cycloalkyl or cycloalkenyl radicals can be substituted by one to five halogen atoms as mentioned above, in particular fluorine or chlorine and/or one of the following radicals: $C_1$–$C_4$-alkyl, $C_1$–$C_4$-alkoxy, $C_1$–$C_4$-alkylthio, cyano, $C_1$–$C_4$-alkylcarbonyl, $C_1$–$C_4$-alkoxycarbonyl or phenyl, such as mentioned above in general and particular;

$C_3$–$C_6$-alkenyl or $C_3$–$C_6$-alkynyl as mentioned in the case of $R^1$, which can carry one to five halogen atoms as mentioned above, in particular fluorine or chlorine and/or one of the following radicals:

$C_1$–$C_4$-alkyl, $C_1$–$C_4$-alkoxy, $C_1$–$C_4$-alkylthio, cyano, $C_1$–$C_4$-alkylcarbonyl, $C_1$–$C_4$-alkoxycarbonyl or phenyl, as mentioned above in general and particular;

$R^4$ is further a 5- or 6-membered heteroaryl such as furyl, thienyl, pyrryl, pyrazolyl, imidazolyl, triazolyl, isoxazolyl, oxazolyl, isothiazolyl, thiazolyl, thiadiazolyl, pyridyl, pyrimidinyl, pyrazinyl, pyridazinyl, triazinyl, for example 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 5-thiazolyl, 2-imidazolyl, 4-imidazolyl, 5-imidazolyl, 2-pyrrolyl, 3-pyrrolyl, 4-pyrrolyl, 3-pyrazolyl, 4-pyrazolyl, 5-pyrazolyl, 2-pyridyl, 3-pyridyl, 4-pyridyl, oxa-2,4-diazolyl, oxa-3,4-diazolyl, thia-2,4-diazolyl, thia-3,4-diazolyl and triazolyl, where the heteroaryl rings can carry one to five halogen atoms as mentioned above, in particular fluorine or chlorine and/or one of the following radicals: nitro, cyano, hydroxyl, mercapto, amino, $C_1$–$C_4$-haloalkyl, $C_1$–$C_4$-haloalkoxy, $C_1$–$C_4$-alkylamino, $C_1$–$C_4$-alkyl, $C_1$–$C_4$-alkoxy, $C_1$–$C_4$-alkylthio, di-$C_1$–$C_4$-alkylamino, $C_1$–$C_4$-alkylcarbonyl, $C_1$–$C_4$-alkoxycarbonyl or phenyl, as mentioned above in general and particular;

$R^4$ is further phenyl or naphthyl, which can be substituted by one or more of the following radicals: halogen, nitro, cyano, hydroxyl, mercapto, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, amino, $C_1$–$C_4$-alkylamino, $C_1$–$C_4$-dialkylamino, $C_1$–$C_4$-alkylcarbonyl or $C_1$–$C_4$-alkoxycarbonyl, in particular as mentioned above, and also 1-naphthyl, 2-naphthyl, 3-bromo-2-naphthyl, 4-methyl-1-naphthyl, 5-methoxy-1-naphthyl, 6-trifluoromethyl-1-naphthyl, 7-chloro-1-naphthyl, 8-hydroxy-1-naphthyl;

or $R^4$ with $R^5$, together with the adjacent carbon atom, forms a 3- to 8-membered ring which can contain an oxygen or sulfur atom, and is unsubstituted or, depending on ring size, carries one to three of the following radicals:

$C_1$–$C_4$-alkyl, $C_1$–$C_4$-alkoxy, $C_1$–$C_4$-haloalkyl, $C_1$–$C_4$-haloalkoxy, $C_1$–$C_4$-alkylthio as mentioned above in general and particular;

$R^5$ is hydrogen, $C_1$–$C_4$-alkyl, $C_3$–$C_6$-alkenyl, $C_3$–$C_6$-alkynyl, $C_1$–$C_4$-alkylcarbonyl, $C_3$–$C_8$-cycloalkyl, $C_1$–$C_4$-haloalkyl, $C_1$–$C_4$-alkoxyalkyl, $C_1$–$C_4$-alkoxycarbonyl, $C_1$–$C_4$-alkylthioalkyl or phenyl, or $R^5$ with $R^4$ forms a 3- to 6-membered ring as indicated above;

Y is sulfur, oxygen or a single bond;

Ⓝ is a) a radical —$N_3$, —NC, —NCS or —NCO;

b) a radical

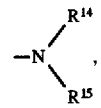

where $R^{14}$ and $R^{15}$, which can be identical or different, are:

hydrogen;

$C_1$–$C_4$-alkyl, $C_3$–$C_6$-alkenyl, $C_3$–$C_6$-alkynyl, $C_3$–$C_8$-cycloalkyl such as mentioned in particular in the case of $R^1$, where these radicals can carry one to five halogen atoms and/or one or two of the following radicals: $C_1$–$C_4$-alkoxy, $C_1$–$C_4$-haloalkoxy, $C_1$–$C_4$-alkylthio, $C_1$–$C_4$-alkylcarbonyl, $C_1$–$C_4$-alkoxycarbonyl or unsubstituted or substituted phenyl such as mentioned in particular above; phenyl which is unsubstituted or substituted as mentioned in the case of $R^1$;

or $R^{14}$ and $R^{15}$ together form an unsubstituted or substituted $C_4$–$C_7$-alkylene chain which is closed to give a ring or an unsubstituted or substituted $C_3$–$C_6$-alkylene chain which is closed to give a ring and which has a heteroatom selected from the group consisting of oxygen, sulfur and nitrogen, such as mentioned in particular in the case of $R^6$ and $R^7$;

c) a radical

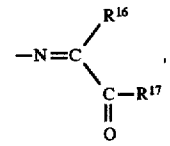

where the radicals have the following meanings:

$R^{16}$ is hydrogen, $C_1$–$C_4$-alkyl, $C_1$–$C_4$-haloalkyl, $C_3$–$C_6$-alkenyl, $C_3$–$C_6$-alkynyl, $C_3$–$C_8$-cycloalkyl or unsubstituted or substituted phenyl, such as mentioned in particular in the case of $R^1$;

$R^{17}$ is hydrogen or the abovementioned, unsubstituted or substituted alkyl, haloalkyl, alkenyl, alkynyl, cycloalkyl or phenyl radicals;

a radical $OR^{18}$, where $R^{18}$ is $C_1$–$C_4$-alkyl, $C_1$–$C_4$-haloalkyl, $C_3$–$C_6$-alkenyl, $C_3$–$C_6$-alkynyl, $C_3$–$C_8$-cycloalkyl or unsubstituted or substituted phenyl, such as mentioned in particular in the case of $R^1$;

a radical —$NR^{14}R^{15}$, as defined above;

d) a radical

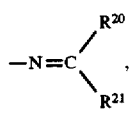

where $R^{20}$ and $R^{21}$, which can be identical or different, are:

C$_1$–C$_4$-alkyl, C$_3$–C$_6$-alkenyl, C$_3$–C$_6$-alkynyl, C$_3$–C$_8$-cycloalkyl as mentioned above, where these radicals can each carry one to five halogen atoms and/or one or two of the following radicals:

C$_1$–C$_4$-alkoxy, C$_1$–C$_4$-haloalkoxy, C$_1$–C$_4$-alkylthio, C$_1$–C$_4$-alkylcarbonyl, C$_1$–C$_4$-alkoxycarbonyl or unsubstituted or substituted phenyl, such as mentioned in particular above;

phenyl, which can be substituted as mentioned in particular in the case of $R^1$;

or $R^{20}$ and $R^{21}$ together form an unsubstituted or substituted C$_4$–C$_7$-alkylene chain which is closed to give a ring or together form an unsubstituted or substituted C$_3$–C$_6$-alkylene chain which is closed to give a ring and has a heteroatom selected from the group consisting of oxygen, sulfur and nitrogen, such as mentioned in particular in the case of $R^6$ and $R^7$;

e) a radical

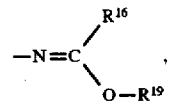

where $R^{16}$ and $R^{19}$, which can be identical or different, are hydrogen or the unsubstituted or substituted alkyl, haloalkyl, alkenyl, alkynyl or phenyl groups mentioned in the case of $R^1$;

f) a radical

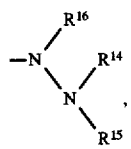

where $R^{14}$, $R^{15}$ and $R^{16}$ are defined as mentioned above.

Particularly preferred lactic acid derivatives are those of the formula I, in which a) $R^2$ and $R^3$ are methoxy and X is CH, b) $R^2$ and $R^3$ are methoxy, X is CH and $R^5$ is methyl, c) $R^2$ and $R^3$ are methoxy, X is CH, $R^1$ is OR$^9$ and Ⓝ is —N$_3$, d) $R^2$ and $R^3$ are methoxy, X is CH, $R^1$ is OR$^9$ and Ⓝ is —NR$^{14}$R$^{15}$, e) $R^2$ and $R^3$ are methoxy, X is CH, $R^1$ is OR$^9$ and Ⓝ is —N(R$^{16}$)(COR$^{17}$).

In the following table, some of the preferred compounds are listed by way of example. The groups mentioned therein for a substituent are additionally considered per se, independently of the specific combination with other substituents in which they are mentioned, to be a particularly preferred definition of the substituent concerned.

| R$^1$ | R$^4$ | R$^5$ | A | R$^2$ | R$^3$ | X | Y |
|---|---|---|---|---|---|---|---|
| OCH$_3$ | Phenyl | Methyl | N$_3$ | OCH$_3$ | OCH$_3$ | CH | O |
| OH | Phenyl | Methyl | N$_3$ | OCH$_3$ | OCH$_3$ | CH | O |
| OH | Phenyl | Methyl | N$_3$ | OCH$_3$ | O—CH$_2$—CH$_2$— | | O |
| OH | Phenyl | Methyl | N$_3$ | OCH$_3$ | OCH$_3$ | N | O |
| OH | Phenyl | Methyl | N$_3$ | OCH$_3$ | OCH$_3$ | CH | S |
| OH | Phenyl | Methyl | N$_3$ | OCH$_3$ | OCH$_3$ | N | S |
| OH | Methyl | Methyl | N$_3$ | OCH$_3$ | OCH$_3$ | CH | O |
| OH | Phenyl | H | N$_3$ | OCH$_3$ | OCH$_3$ | CH | O |
| OH | Phenyl | i-Propyl | NH—C(=O)—CH$_3$ | OCH$_3$ | OCH$_3$ | CH | O |
| OH | Methyl | Methyl | NH—C(=O)—CH$_2$CH$_3$ | OCH$_3$ | OCH$_3$ | CH | O |
| OH | —(CH$_2$)$_5$— | | NH—C(=O)—Ph | OCH$_3$ | OCH$_3$ | CH | O |
| OH | Phenyl | Methyl | NH—Ph | OCH$_3$ | OCH$_3$ | CH | O |
| OH | 2-Thienyl | Methyl | NH—(2-Cl-Ph) | OCH$_3$ | OCH$_3$ | CH | O |

-continued

| R¹ | R⁴ | R⁵ | A | R² | R³ | X | Y |
|---|---|---|---|---|---|---|---|
| OH | Phenyl | Methyl | NH₂ | OCH₃ | OCH₃ | CH | O |
| OCH₃ | 2-Fluorophenyl | Ethyl | NHCH₃ | OCH₃ | OCH₃ | CH | O |
| OC₂H₅ | 3-Chlorophenyl | Propyl | NHC₂H₅ | OCH₃ | OCH₃ | N | O |
| ON(CH₃)₂ | 4-Bromophenyl | i-Propyl | N(CH₃)₂ | CF₃ | CF₃ | CH | S |
| ON=C(CH₃)₂ | 3-Thienyl | Methyl | N(CH₃)(C₂H₅) | OCF₃ | OCF₃ | CH | O |
| NHSO₂C₆H₅ | 3-Thienyl | Methyl | NH-i-C₃H₇ | CH₃ | CH₃ | CH | O |
| NHPhenyl | 2-Furyl | Methyl | N(i-C₃H₇)₂ | Cl | Cl | CH | O |
| ONa | 3-Furyl | Methyl | NC | OCH₃ | O—CH₂CH₂— | | S |
| O—CH₂—C≡CH | Phenyl | Ethyl | NH₂ | OCH₃ | CF₃ | CH | O |
| OH | Phenyl | Propyl | NCS | OCH₃ | OCF₃ | CH | O |
| OCH₃ | Phenyl | i-Propyl | NCO | OCH₃ | CH₃ | CH | O |
| OC₂H₅ | Phenyl | Methyl | piperidinyl (N-ring) | OCH₃ | Cl | CH | S |
| ON(CH₃)₂ | 2-Methylphenyl | Methyl | morpholinyl | OCH₃ | OCH₃ | CH | O |
| ON=C(CH₃)₂ | 3-Methoxyphenyl | Methyl | NH-cyclopropyl | OCH₃ | OCH₃ | CH | O |
| NHSO₂C₆H₅ | 4-Nitrophenyl | Methyl | NH-cyclopentyl | OCH₃ | OCH₃ | CH | O |
| NHPhenyl | Methyl | Methyl | N(CH₃)(cyC₆H₁₁) | CF₃ | CF₃ | N | S |
| ONa | Methyl | Methyl | NH(CH₂—CH=CH₂) | OCF₃ | OCF₃ | N | O |
| O—CH₂—C≡CH | Methyl | Methyl | N(C₂H₅)(CH₂—C≡CH) | CH₃ | CH₃ | N | O |
| OH | Methyl | Methyl | NH—C₆H₄—CH₃ | Cl | Cl | N | O |
| OCH₃ | Phenyl | Methyl | NH—COOC(CH₃)₃ | OCH₃ | O—CH₂—CH₂ | | O |
| OC₂H₅ | Phenyl | Methyl | NH—COOC₆H₅ | OCH₃ | CF₃ | N | S |
| ON(CH₃)₂ | Phenyl | Methyl | N(CH₃)C—COOC₂H₅ | OCH₃ | OCF₃ | N | O |
| ON=C(CH₃)₂ | 2-Hydroxyphenyl | Methyl | NHCH₂C₆H₅ | OCH₃ | CH₃ | N | O |
| NHSO₂C₆H₅ | 3-Trifluoro-methylphenyl | Methyl | N(C₂H₅)—COOCH₂C₆H₅ | OCH₃ | Cl | N | O |
| NHPhenyl | 4-Dimethyl-aminophenyl | Methyl | NH—C(O)—N(CH₃)₂ | OCH₃ | OCH₃ | CH | S |
| ONa | 3-Imidazolyl | Ethyl | NH—C(O)—NH(C₂H₅) | OCH₃ | OCH₃ | CH | S |
| O—CH₂—C≡CH | 4-Imidazolyl | Propyl | N(CH₃)C(O)—NHC(CH₃)₃ | OCH₃ | OCH₃ | N | S |
| OH | 2-Pyrazolyl | i-Propyl | NH—C(O)—N(piperidinyl) | CF₃ | CF₃ | CH | O |
| OCH₃ | 4-Pyrazolyl | Methyl | NH—C(O)—NH₂ | OCF₃ | OCF₃ | CH | O |
| OCH₃ | Phenyl | Methyl | N=C(CH₃)₂ | OCH₃ | OCH₃ | CH | O |
| OH | Phenyl | Methyl | N=CH—C₂H₅ | OCH₃ | OCH₃ | CH | O |
| OH | Phenyl | Methyl | N=CH—C₆H₅ | OCH₃ | O—CH₂—CH₂— | | O |
| OH | Phenyl | Methyl | N=C(CH₃)—C₆H₅ | OCH₃ | OCH₃ | N | O |
| OH | Phenyl | Methyl | N=C(CH₃)—C₆H₅ | OCH₃ | OCH₃ | CH | S |

-continued

| R¹ | R⁴ | R⁵ | A | R² | R³ | X | Y |
|---|---|---|---|---|---|---|---|
| OH | Phenyl | Methyl | 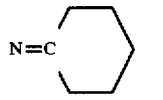 N=C-cyclohexyl | OCH₃ | OCH₃ | CH | S |
| OH | Phenyl | Methyl | 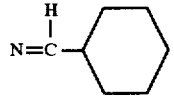 N=CH-cyclohexyl | OCH₃ | OCH₃ | CH | O |
| OH | Phenyl | Methyl | NH—OH | OCH₃ | OCH₃ | CH | O |
| OH | Phenyl | H | NH—OCH₃ | OCH₃ | OCH₃ | CH | O |
| OH | Phenyl | i-Propyl | N(CH₃)(OC₂H₅) | OCH₃ | OCH₃ | CH | O |
| OH | Methyl | Methyl | NH—OC₆H₅ | OCH₃ | OCH₃ | CH | O |
| OH | —(CH₂)₅— | | N(CH₃)—OC(CH₃)₃ | OCH₃ | OCH₃ | CH | O |
| OH | Phenyl | Methyl | NH—O—CH₂—C₆H₅ | OCH₃ | OCH₃ | CH | O |
| OH | 2-Thienyl | Methyl | NH-NH₂ | OCH₃ | OCH₃ | CH | O |
| OH | Phenyl | Methyl | NH-N(CH₃)₂ | OCH₃ | OCH₃ | CH | O |
| OCH₃ | 2-Fluorophenyl | Ethyl | N(CH₃)—NH₂ | OCH₃ | OCH₃ | CH | O |
| OC₂H₅ | 3-Chlorophenyl | Propyl | NH-NH(C₂H₅) | CF₃ | CF₃ | N | O |
| ON(CH₃)₂ | 4-Bromophenyl | i-Propyl | N(CH₃)—N(CH₃)(CH₂C₆H₅) | CF₃ | CF₃ | CH | S |
| ON=C(CH₃)₂ | 2-Thienyl | Methyl | 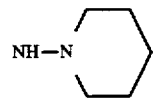 NH—N-piperidyl | OCF₃ | OCF₃ | CH | O |
| NHSO₂C₆H₅ | 3-Thienyl | Methyl | 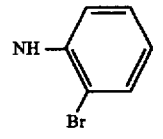 NH-(2-bromophenyl) | CH₃ | CH₃ | CH | O |
| NHPhenyl | 2-Furyl | Methyl | 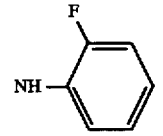 NH-(2-fluorophenyl) | Cl | Cl | CH | O |
| ONa | 3-Furyl | Methyl | 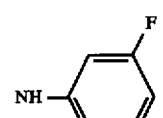 NH-(3-fluorophenyl) | OCH₃ | O—CH₂—CH₂ | | S |
| O—CH₂≡CH | Phenyl | Ethyl | 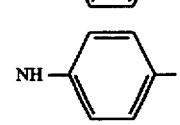 NH-(4-fluorophenyl) | OCH₃ | CF₃ | CH | |
| OH | Phenyl | Propyl | N(CH₃)CO—CH₃ | OCH₃ | OCF₃ | CH | O |
| OCH₃ | Phenyl | i-Propyl | NH-CO—CH₂C₆H₅ | OCH₃ | CH₃ | CH | O |
| OC₂H₅ | Phenyl | Methyl | (CH₃)₂—N—CO—CH₃ | OCH₃ | Cl | CH | S |
| ON(CH₃)₂ | 2-Methylphenyl | Methyl | N(C₂H₅)CO—CH₃ | OCH₃ | OCH₃ | CH | O |
| ON=C(CH₃)₂ | 3-Methoxyphenyl | Methyl | 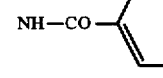 NH—CO-(4-methylphenyl) | OCH₃ | OCH₃ | CH | O |
| NHSO₂C₆H₅ | 4-Nitrophenyl | Methyl | 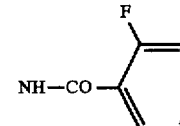 NH—CO-(2-fluorophenyl) | OCH₃ | OCH₃ | CH | O |
| NHPhenyl | Methyl | Methyl | 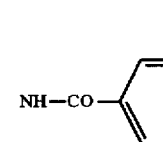 NH—CO-(3-chlorophenyl) | CF₃ | CF₃ | N | S |

-continued

| $R^1$ | $R^4$ | $R^5$ | A | $R^2$ | $R^3$ | X | Y |
|---|---|---|---|---|---|---|---|
| ONa | Methyl | Methyl | $N(CH_3)-CO-C_6H_5$ | $OCF_3$ | $OCF_3$ | N | O |
| $O-CH_2-C\equiv CH$ | Methyl | Methyl | $NH-CO-C(CH_3)_3$ | $CH_3$ | $CH_3$ | N | O |
| OH | Methyl | Methyl | NC | Cl | Cl | N | O |
| $OCH_3$ | Phenyl | Methyl | NCS | $OCH_3$ | $O-CH_2-CH_2$ | | O |
| $OC_2H_5$ | Phenyl | Methyl | NCO | $OCH_3$ | $CF_3$ | N | S |
| $ON(CH_3)_2$ | Phenyl | Methyl | $NH_2$ | $OCH_3$ | $OCF_3$ | N | O |
| $ON=C(CH_3)_2$ | 2-Hydroxyphenyl | Methyl | NH—CO—⬡ | $OCH_3$ | $CH_3$ | N | O |
| $NHSO_2C_6H_5$ | 3-Trifluoromethylphenyl | Methyl | NH—CO—△ | $OCH_3$ | Cl | N | O |
| NHPhenyl | 4-Dimethylaminophenyl | Methyl | $NH-CO-CF_3$ | $OCH_3$ | $OCH_3$ | CH | S |
| ONa | 3-Imidazolyl | Ethyl | $N_3$ | $OCH_3$ | $OCH_3$ | CH | S |
| $O-CH_2-C\equiv CH$ | 4-Imidazolyl | Propyl | $N_3$ | $OCH_3$ | $OCH_3$ | N | S |
| OH | 2-Pyrazolyl | i-Propyl | $N_3$ | $CF_3$ | $CF_3$ | CH | O |
| $OCH_3$ | 4-Pyrazolyl | Methyl | $N_3$ | $OCF_3$ | $OCF_3$ | CH | O |

The substituted lactic acid derivatives I are also suitable as antidotes for making herbicidal active compounds more tolerable for crop plants such as cultivated millet, rice, corn, types of cereal (wheat, rye, barley, oats), cotton, sugar beet, sugar cane and soybeans. They act antagonistically on herbicides of very different classes of substance such as triazines, phenylurea derivatives, carbamates, thiocarbamates, haloacetanilides, benzoic acid derivatives and, in particular, halophenoxyacetic acid esters, substituted phenoxyphenoxyacetic acid esters, phenoxyphenoxypropionic acid esters and cyclohexenone derivatives.

Herbicidally active cyclohexenone derivatives XIII are disclosed, for example, in EP-A 228 598, EP-A 230 235, EP-A 238 021, EP-A 368 227, U.S. Pat. No. 4,432,786, DE-A 24 39 104, DE-A 38 38 309 and EP-A 537 463. They are used mainly for controlling undesired grasses in dicotyledon crops and in grasses which do not belong to the Gramineae family. Depending on the substituents and the dose of the compounds of the type XIII on application thereof, these cyclohexenones can also be employed for the selective control of undesired grasses in Gramineae crops such as wheat and rice.

For example, the substituents in formula XIII have the meanings mentioned in EP-A 537 463, such as:

$R^a$ is a $C_1-C_6$-alkyl group;

$R^b$ is hydrogen, the equivalent of an agriculturally utilizable cation, a $C_2-C_8$-alkylcarbonyl group, a $C_1-C_{10}$-alkylsulfonyl group, a $C_1-C_{10}$-alkylphosphonyl group or the benzoyl, benzenesulfonyl or benzenephosphonyl group, where the three last-mentioned groups can additionally each carry 1 to 5 halogen atoms;

$R^c$ is hydrogen, the cyano group, the formyl group, a $C_1-C_6$alkyl group, a $C_1-C_4$-alkoxy-$C_1-C_6$-alkyl or $C_1-C_4$-alkylthio-$C_1-C_6$-alkyl group, a phenoxy-$C_1-C_6$-alkyl, phenylthio-$C_1-C_6$-alkyl, pyridyloxy-$C_1-C_6$-alkyl or pyridylthio-$C_1-C_6$-alkyl group, where the phenyl and pyridyl rings can each additionally carry one to three radicals selected from a group consisting of nitro, cyano, halogen, $C_1-C_4$-alkyl, partially or completely halogenated $C_1-C_4$-alkyl, $C_1-C_4$-alkoxy, partially or completely halogenated $C_1-C_4$-alkoxy, $C_1-C_4$-alkylthio, $C_3-C_6$-alkenyl, $C_3-C_6$-alkenyloxy, $C_3-C_6$-alkynyl, $C_3-C_6$-alkynyloxy and $—NR^gR^h$, where $R^g$ is hydrogen, $C_1-C_4$-alkyl, $C_3-C_6$-alkenyl, $C_3-C_6$-alkynyl, $C_1-C_6$-acyl or benzoyl, which can carry one to three radicals selected from a group consisting of nitro, cyano, halogen, $C_1-C_4$-alkyl, partially or completely halogenated $C_1-C_4$-alkyl, $C_1-C_4$-alkoxy and $C_1-C_4$-alkylthio, and $R^h$ is hydrogen, $C_1-C_4$-alkyl, $C_3-C_6$-alkenyl or $C_3-C_6$-alkynyl;

a $C_3-C_7$-cycloalkyl or a $C_5-C_7$-cycloalkenyl group, where these groups can additionally carry one to three radicals selected from a group consisting of hydroxyl, halogen, $C_1-C_4$-alkyl, partially or completely halogenated $C_1-C_4$-alkyl, $C_1-C_4$-alkoxy, $C_1-C_4$-alkylthio, benzylthio, $C_1-C_4$-alkylsulfonyl, $C_1-C_4$-alkylsulfenyl and $C_1-C_4$-alkylsulfinyl, a 5-membered saturated heterocycle which contains one or two oxygen or sulfur atoms or an oxygen and a sulfur atom as heteroatoms, and which additionally can carry one to three radicals selected from a group consisting of $C_1-C_4$-alkyl, partially or completely halogenated $C_1-C_4$-alkyl, $C_1-C_4$-alkoxy and $C_1-C_4$-alkylthio, a 6- or 7-membered saturated or mono- or diunsaturated heterocycle which contains one or two oxygen or sulfur atoms or an oxygen or a sulfur atom as heteroatoms, and which additionally can carry one to three radicals selected from a group consisting of hydroxyl, halogen, $C_1-C_4$-alkyl, partially or completely halogenated $C_1-C_4$-alkyl, $C_1-C_4$-alkoxy, $C_1-C_4$-alkylthio, a 5-membered heteroaromatic, containing one to three heteroatoms selected from a group consisting of one or two nitrogen atoms and an oxygen or sulfur atom, where the heteroaromatic can additionally carry one to three radicals selected from a group consisting of cyano, halogen, $C_1-C_4$-alkyl, partially or completely halogenated $C_1-C_4$-alkyl, $C_1-C_4$-alkoxy, partially or completely halogenated $C_1-C_4$-alkoxy, $C_1-C_4$-alkylthio, $C_2-C_6$-alkenyl, $C_2-C_6$-alkenyloxy, $C_3-C_6$-alkynyloxy and $C_1-C_4$-alkoxy-$C_1-C_4$-alkyl, a phenyl or pyridyl group, which each additionally can carry one to three radicals selected from a group consisting of nitro, cyano, formyl, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_6$-alkenyl, $C_3$–$C_6$-alkenyloxy, $C_3$–$C_6$-alkynyl, $C_3$–$C_6$-alkynyloxy and —$NR^kR^l$, where $R^k$ and $R^l$ have the abovementioned meanings;

$R^d$ is hydrogen, the hydroxyl group or, if $R^c$ is a $C_1$–$C_6$-alkyl group, is a $C_1$–$C_6$-alkyl group;

$R^e$ is hydrogen, halogen, the cyano group, a $C_1$–$C_4$-alkoxycarbonyl group or a $C_1$–$C_4$-alkylketoxime group;

w is a $C_1$–$C_6$-alkylene, $C_3$–$C_6$-alkenylene or $C_3$–$C_6$-alkynylene chain, which each additionally can carry one to three radicals selected from a group consisting of one to three $C_1$–$C_3$-alkyl substituents, one to three halogen atoms and a methylene substituent;

a $C_3$–$C_6$-alkylene or $C_4$–$C_6$-alkenylene chain which both additionally can carry one to three $C_1$–$C_3$-alkyl radicals, where in each case one methylene group of the chains can be substituted by an oxygen or sulfur atom, a sulfoxide or sulfone group or a group —N($R^i$)—, where $R^i$ is hydrogen, $C_1$–$C_4$-alkyl, $C_3$–$C_6$-alkenyl or $C_3$–$C_6$-alkynyl;

$R^i$ is hydrogen; the vinyl group;

$R^f$ is a group —CH=CH—Z, where Z is cyano, halogen, a $C_1$–$C_4$-alkyl radical, a partially or completely halogenated $C_1$–$C_4$-alkyl radical, a $C_3$–$C_6$-cycloalkyl radical, which for its part can additionally carry one to three substituents selected from a group consisting of hydroxyl, halogen, $C_1$–$C_4$-alkyl, partially or completely halogenated $C_1$–$C_4$-alkyl and $C_1$–$C_4$-alkoxy;

the carboxyl radical, a $C_1$–$C_8$-alkoxycarbonyl radical, the benzyloxycarbonyl radical, the phenyl, thienyl or pyridyl radical, where these three aromatic radicals can each additionally carry one to three substituents selected from a group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_1$–$C_4$-alkylthio, $C_3$–$C_6$-cycloalkyl where the cycloalkyl substituent for its part can additionally carry one to three radicals selected from a group consisting of halogen, $C_1$–$C_4$-alkyl, partially or completely halogenated $C_1$–$C_4$-alkyl and $C_1$–$C_4$-alkoxy;

the ethynyl group, which can carry one of the following radicals: a $C_1$–$C_4$-alkyl or $C_3$–$C_6$-cycloalkyl radical which both additionally can carry one to three substituents selected from a group consisting of hydroxyl, halogen, $C_1$–$C_4$-alkyl, partially or completely halogenated $C_1$–$C_4$-alkyl and $C_1$–$C_4$-alkoxy, or the phenyl, thienyl or pyridyl radical, where the aromatic radicals can each additionally carry one to three substituents selected from a group consisting of nitro, cyano, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy and $C_1$–$C_4$-alkylthio;

the phenyl group, a halophenyl group, a dihalophenyl group, a 5-membered heteroaromatic group having one to three heteroatoms selected from a group consisting of one to three nitrogen atoms and an oxygen or sulfur atom, or a 6-membered heteroaromatic group having one to four nitrogen atoms which cannot all simultaneously be adjacent, where the phenyl and heteroaryl groups additionally can carry one to three radicals selected from a group consisting of nitro, $C_1$–$C_4$-alkoxy radicals, $C_1$–$C_4$-alkylthio radicals, partially or completely halogenated $C_1$–$C_4$-alkoxy radicals, radicals Z or a radical —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl, which additionally can carry one to three substituents selected from a group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio.

The preparation of these cyclohexenone derivatives and their application can be carried out as indicated in EP-A-537 463.

Among the cyclohexenone oxime ethers of the formula XIII, the compounds emphasized in EP-A 537 463, in Tables 1–8, are of particular interest. With respect to their economical importance, mixtures of the lactic acid derivatives I with the following cyclohexenone derivatives are particularly preferred:

| No. | Notation |
| --- | --- |
| XIII.1 | 2-(1-ethoximinobutyl)-5-(2-ethylthiopropyl)-cyclohexane-1,3-dione [Trade name: Poast ®]; |
| XIII.2 | 2-[1-(trans-3-chloroallyloximino)butyl]-5-(2-ethylthiopropyl)cyclohexane-1,3-dione [Trade name: Select ®]; |
| XIII.3 | 2-(1-ethoximinobutyl)-5-mesitylcyclohexane-1,3-dione [Trade name: Grasp ®]; |
| XIII.4 | 2-(1-ethoximinobutyl)-5-tetrahydrothiopyran-3-yl-cyclohexane-1,3-dione [Trade name: Focus ®]; |
| XIII.5 | 2-[1-(trans-3-chloroallyloximino)propyl]-5-tetrahydropyran-4-yl-cyclohexane-1,3-dione; |
| XIII.6 | 2-[1-(trans-3-chloroallyloximino)propyl]-5-(1-methylthiocyclopropyl)cyclohexane-1,3-dione; |
| XIII.7 | 2-{1-[4-(4-chlorophenyl)but-3-enyloximino]-propyl}-5-tetrahydrothiopyran-3-yl-cyclohexane-1,3-dione; |
| XIII.8 | 2-{1-[4-(4-fluorophenyl)but-3-enyloximino]-propyl}-5-tetrahydrothiopyran-3-yl-cyclohexane-1,3-dione; |
| XIII.9 | 2-{1-[2-(4-chlorophenoxy)propyloximino]-butyl}-5-tetrahydrothiopyran-3-yl-cyclohexane-1,3-dione. |

As herbicides, the compounds I or the compositions containing them and their environmentally tolerable salts e.g. of alkali metals and alkaline earth metals can very effectively control broad-leafed weeds and grass weeds in crops such as wheat, rice, corn, soybeans and cotton without damaging the crop plants, an effect which occurs especially even at low application rates.

The compounds I or the herbicidal compositions containing them can be applied by spraying, atomizing, dusting, broadcasting or watering, for example in the form of directly sprayable aqueous solutions, powders, suspensions, even high-percentage aqueous, oily or other suspensions or dispersions, emulsions, oil dispersions, pastes, dusting compositions, broadcasting compositions or granules. The application forms depend on the intended uses; in each case they should if possible ensure the finest dispersion of the active compounds according to the invention.

The compounds I are generally suitable for preparing directly sprayable solutions, emulsions, pastes or oil dispersions. Suitable inert additives are mineral oil fractions of medium to high boiling point, such as kerosene or diesel oil, additionally coal tar oils and oils of vegetable or animal origin, aliphatic, cyclic and aromatic hydrocarbons, e.g. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agent, adhesive, dispersant or emulsifier and possibly solvent or oil can also be prepared, which are suitable for dilution with water.

Suitable surface-active substances are the alkali metal, alkaline earth metal and ammonium salts of aromatic sulfonic acids, e.g. lignosulfonic, phenolsulfonic, naphthalenesulfonic and dibutylnaphthalenesulfonic acid, as well as of fatty acids, alkyl- and alkylarylsulfonates, alkyl, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenyl ether, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, e.g. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (by NMR spectrum).

The compounds I according to the invention can be formulated, for example, as follows:

I. 20 parts by weight of the compound No. 1.2 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of the compound No. 1.6 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of the active compound No. 1.2 are dissolved in a mixture which consists of 25 parts by weight of cyclohexanone, 65 parts by weight of a mineral oil fraction of boiling point 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of the active compound No. 1.6 are mixed well with 3 parts by weight of the sodium salt of diisobutylnaphthalene α-sulfnic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

V. 3 parts by weight of the active compound No. 1.2 are mixed with 97 parts by weight of finely divided kaolin. In this way a dusting composition is obtained which contains 3% by weight of the active compound.

VI. 20 parts by weight of the active compound No. 1.6 are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the herbicidal compositions or of the active compounds can be carried out pre-emergence or post-emergence. If the active compounds are less tolerable for certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

Depending on the target of control, time of year, target plants and stage of growth, the application rates of active compound are from 0.001 to 10.0, preferably from 0.01 to 3.0, kg/ha of active substance (a.s.).

In consideration of the variety of application methods, the compounds I according to the invention or compositions containing them can additionally be employed in a further number of crop plants for the elimination of undesired plants. Suitable crops are, for example, the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cyn-*

*odon dactylon, Daucus carota, Elaeis guineensis, Fragaria vesca, Glycine max, Gossypium hirsutum (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N. rustica), Olea europaea, Oryza sativa, Phaseolus lunatus, Phaseolus vulgaris, Picea abies, Pinus* spp., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

Moreover, the compounds I can also be employed in crops which have been made largely resistant to the action of I or other herbicides by breeding and/or by means of genetic engineering methods.

The compounds of the formula I can furthermore affect the various stages of development of a plant and are therefore employed as growth regulators. The varied action of the plant growth regulators is especially dependent a) on the plant species and variety;

b) on the time of application, relative to the stage of development of the plant, and on the time of year;

c) on the type of application and application process (e.g. seed-dressing, soil treatment, foliar application or stem injection in the case of trees);

d) on climatic factors (e.g. temperature, amount of precipitation, additionally length of day and light intensity);

e) on the soil condition (including fertilization);

f) on the formulation and application form of the active compound and g) on the concentrations of the active substance used.

A few of the number of different possibilities for application of the plant growth regulators of the formula I according to the invention in plant cultivation, in agriculture and in horticulture are mentioned below:

A. The vegetative growth of the plants can be severely inhibited by the compounds which can be used according to the invention, which is manifested in particular in a reduction in the longitudinal growth. The treated plants accordingly exhibit stocky growth; additionally darker leaf coloration is to be observed.

A decreased intensity in the growth of grasses on roadsides, hedgerows, canal banks and on plots of grass such as parks, sports grounds and orchards, ornamental lawns and airfields proves to be advantageous in practice, so that the labor- and cost-intensive mowing can be reduced.

The increase in the resistance of crops susceptible to lodging, such as cereals, corn, sunflowers and soybeans, is also of economic interest. The culm shortening and culm strengthening caused in this case decrease or eliminate the danger of lodging (of being bent over) of plants under unfavorable weather conditions before harvesting.

The application of growth regulators for inhibiting the longitudinal growth and for temporally altering the course of ripening in cotton is also important. Completely mechanized harvesting of this important crop plant is thus made possible.

In the case of fruit and other trees, pruning costs can be saved using the growth regulators. In addition, the alternation of fruit trees can be broken by means of growth regulators.

The lateral branching of the plants can also be increased or inhibited by application of growth regulators. There is interest in this if, e.g. in the case of tobacco plants, the formation of side shoots (suckers) is to be inhibited in favor of leaf growth.

In the case of winter rape, for example, the frost resistance can also be considerably increased using growth regulators. In this case, on the one hand, the longitudinal growth and the development of an excessively luxuriant (and thereby particularly frost-susceptible) herbage or biomass are inhibited. On the other hand, after sowing and before the winter frosts set in, the young rape plants are held back in the vegetative development stage despite favorable growth conditions. As a result, the frost danger to those plants which are prone to premature degeneration of the inhibition of flowering and to transition into the generative phase is eliminated. Even in other crops, e.g. winter cereals, it is advantageous if the populations are indeed well tillered by treatment with compounds according to the invention in the autumn, but are not too luxuriant when going into the winter. As a result, the increased frost sensitivity and, because of the relatively low herbage or biomass, attack by various diseases (e.g. fungal disease) can be prevented. The inhibition of the vegetative growth additionally makes possible a more compact planting of the soil with many crop plants, so that an additional yield can be achieved, based on the soil area.

B. Additional yields both of parts of plants and of plant constituents can be achieved using the growth regulators. Thus it is possible, for example, to induce the growth of greater amounts of buds, flowers, leaves, fruit, seeds, roots and tubers, to increase the content of sugar in sugar beet, sugar cane and citrus fruits, to raise the protein content in cereals or soybeans or to stimulate rubber trees to an increased flow of latex.

In this case, the compounds of the formula I can cause increases in yield by intervention in the plant metabolism or by promotion or inhibition of vegetative and/or of generative growth.

C. Finally, both reduction or prolongation of the development stages and acceleration or retardation of the ripening of the harvested parts of plants before or after harvesting can be achieved using plant growth regulators.

Of economic interest, for example, is the facilitation of harvesting, which is made possible by the temporally concentrated fall or decrease in the adhesiveness to the tree in the case of citrus fruits, olives or in the case of other species and varieties of pomes, drupes and indehiscent fruit. The same mechanism, that is the promotion of the formation of abscission tissue between the fruit or leaf and shoot part of the plant, is also essential for a well-controllable defoliation of productive plants such as, for example, cotton.

D. The intensity of irrigation can be reduced by the use of the substances according to the invention and thus a more economical management can be carried out. Under the influence of growth regulators, a better utilization of the water present, for example, occurs because, inter alia, the opening width of the stomata is reduced, a thicker epidermis and cuticle are formed, the root penetration of the soil is improved and the microclimate in the plant population is favorably influenced by a more compact growth.

The compounds I are particularly suitable for culm shortening of crop plants such as barley, rape and wheat.

The growth regulators of the formula I to be used according to the invention can be supplied to the crop plants both from seeds (as seed-dressing agents) and via the soil, i.e. by the roots and, particularly preferably, by spraying over the leaf. The compositions are prepared here in a similar manner to the herbicides (see above).

As a result of the high plant compatibility, the application rate of active compound is not critical. The optimum application rate varies depending on the target of control, time of year, target plants and stages of growth.

To widen the spectrum of action and to achieve synergistic effects, the lactic acid derivatives I can be mixed with numerous representatives of other herbicidal or growth-regulating active compound groups and applied together. For example, suitable herbicidal mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry e.g. a carboxyl or carbimino group in the 2-position, quinolinecarboxylic acid derivatives, imidazolines, sulfonamides, sulfonylureas, aryloxy- and heteroaryloxyphenoxypropionic acids and their salts, esters and amides and others. Suitable growth regulators are in particular chlormequat chloride, ethylene and mepiquat chloride.

It may additionally be useful to apply the compounds I on their own or together in combination with other herbicides or growth regulators and additionally mixed with further crop protection agents, for example with agents for controlling pests or phytopathogenic fungi or bacteria. Additionally of interest is the miscibility with mineral salt solutions which are employed for the elimination of nutritional and trace element deficiencies. Nonphytotoxic oils and oil concentrates can also be added.

The herbicidal active compounds XIII and the compounds I having antidote activity can be applied together or separately after emergence to the leaves and sprouts of the crop plants and undesired plants. Preferably, however, the herbicidal and antidote active compounds are applied simultaneously in the field. In the case of separate application of antidote and herbicidal active compound, the antidote is preferably applied first.

The antidote and herbicidal active compound can be formulated together or separately and is then present in suspended, emulsifiable or soluble form for the preparation of spray compositions.

Antidote effects are also obtained by treatment of the crop plant seeds or the cuttings with the antidote before sowing or before transplanting. The herbicidal active compound is then applied on its own in the customary manner.

In the case of seed treatment, in general amounts of active compound from 0.01 to 10 g, preferably 0.1 to 2 g, per kilogram of seed are required.

In the case of application of the antidote by seed swelling or during treatment of cuttings, solutions are preferably employed which contain the antagonistic compound in a concentration from 1 to 10,000 ppm, in particular from 100 to 10,000 ppm.

In the various plant crops, different amounts of compound I having antidote activity and herbicidal compound III are customarily required, the quantitative ratios being variable within wide ranges. They are dependent on the structure of the cyclohexenone derivatives, the substituted lactic acid derivatives I and the particular plant crop to which the compounds are applied. Suitable quantitative ratios of herbicidal active compound to substituted lactic acid derivatives I having antidote activity are from 1:10 to 1:0.01, preferably from 1:4 to 1:0.1.

The formulations contain from 0.02 to 95% by weight, preferably 0.5 to 90% by weight, of herbicidal active compound and antidote. The application rates of herbicidal active compound are from 0.05 to 1 kg/ha.

SYNTHESIS EXAMPLES

Example 1

Methyl 3-azido-3-phenyl-2-hydroxybutyrate 19.5 g (300 mmol) of sodium azide and 16.0 g (300 mmol) of ammonium chloride are suspended in 400 ml of methanol and treated with 19.2 g (100 mmol) of methyl 3-phenyl-2,3-epoxybutyrate. The mixture is stirred for 9 hours under reflux and for 12 hours at room temperature, the majority of the methanol is distilled off and the residue is treated with 200 ml of water. It is then extracted with ethyl acetate, and the organic phases are dried and concentrated. The residual oil is treated with a little diethyl ether and the crystals formed are filtered off with suction.

Yield: 6.3 g (27%), m.p.: 110°–112° C.

Example 2

Methyl 3-azido-3-phenyl-2-(4,6-dimethoxypyrimidin-2-yl)oxybutyrate 5.9 g (25 mmol) of methyl 3-azido-3-phenyl-2-hydroxybutyrate (Ex. 1) are dissolved in 80 ml of DMF, treated with 1.7 g (12.5 mmol) of potassium carbonate and 5.5 g (25 mmol) of 4,6-dimethoxy-2-methylsulfonylpyrimidine, and stirred for 6 hours at 50° C. and 12 hours at room temperature. The mixture is then poured onto 400 ml of water, and the precipitate formed is filtered off with suction, washed with water and dried. 6.3 g of a white powder are obtained.

Yield: 67.2%, m.p.: 118°–120° C.

Example 3

3-Azido-3-phenyl-2-(4,6-dimethoxypyrimidin-2-yl)oxybutyric acid 4.1 g (11 mmol) of methyl 3-azido-3-phenyl-2-(4,6-dimethoxypyrimidin-2-yl)oxybutyrate (Ex. 2) are dissolved in 100 ml of methanol/THF (1:1) and treated with 13.2 g (33 mmol) of 10% strength sodium hydroxide solution. The mixture is stirred for 6 hours at 50° C. and for 12 hours at room temperature and concentrated on a rotary evaporator. The residue is taken up in 100 ml of water and acidified to pH 2 using 10% strength hydrochloric acid. The resulting precipitate is filtered off with suction, washed with diethyl ether and dried.

Yield: 1.5 g (26%), m.p.: 193°–195° C.

Example 4

Methyl 3-amino-3-phenyl-2-(4,6-dimethoxypyrimidin-2-yl)oxybutyrate 3.7 g (10 mmol) of methyl 3-azido-3-phenyl-2-(4,6-dimethoxypyrimidin-2-yl)oxybutyrate (Ex. 2) are dissolved in 20 ml of methanol/ethyl acetate (1:1), treated with 400 mg of Pd/C 10% and stirred for 6 h under a hydrogen atmosphere. After filtering off the catalyst and concentrating, a colorless oil is obtained which solidifies after a few days.

Example 5

Methyl 3-dimethylamino-3-phenyl-2-(4,6-dimethoxypyrimidin-2-yl)oxybutyrate 8.7 g (25 mmol) of methyl 3-amino-3-phenyl-2-(4,6-dimethoxypyrimidin-2-yl)oxybutyrate (Ex. 4) are dissolved in 50 ml of methanol and treated with 3.4 g (25 mmol) of potassium carbonate and 7 g (50 mmol) of iodomethane. The mixture is stirred for 24 h at room temperature and concentrated on a rotary evaporator and the residue is taken up in 50 ml of water. The solution is extracted with ethyl acetate, the organic phases are dried and the solvent is removed.

Example 6

Methyl 3-N-tert-butoxycarbonylamino-3-phenyl-2-(4,6-dimethoxyyrimidin-2-yl)oxybutyrate 3.5 g (10 mmol) of methyl 3-amino-3-phenyl-2-(4,6-dimethoxyyrimidin-2-yl)oxybutyrate (Ex. 4) are dissolved in 20 ml of ethyl acetate, treated with 2.6 g (12 mmol) of di-tert-butyl dicarbonate and a spatula tipful of 4-dimethylaminopyridine and the mixture is stirred for 12 hours at room temperature. It is washed with 100 ml of water, the organic phase is dried and the solvent is distilled off. A clear oil remains, which slowly crystallizes.

Example 7

Methyl 3-N-phenylamino-3-phenyl-2-hydroxybutyrate 19.2 g (100 mmol) of methyl 3-phenyl-2,3-epoxybutyrate and 28 g (300 mmol) of aniline are heated to 100° C. with stirring for 8 hours. The excess aniline is distilled off in a high vacuum and the residue is purified by flash chromatography (silica gel, n-hexane/ethyl acetate 9:1). 5.0 g of a diastereomer mixture and 1.6 g of a pure isomer are obtained.

Yield: 23.1%, m.p.: 108°–110° C. (1 diastereomer)

Example 8

Methyl 3-N-phenylamino-3-phenyl-2-(4,6-dimethoxypyrimidin-2-yl)oxybutyrate 2.1 g (7.4 mmol) of methyl 3-N-phenylamino-3-phenyl-2-hydroxybutyrate (Ex. 7) are dissolved in 50 ml of DMF, 0.5 g (3.7 mmol) of potassium carbonate and 1.6 g (7.4 mmol) of 4,6-dimethoxy-2-methylsulfonylpyrimidine are added and the mixture is stirred for 6 hours at 50° C., then for 12 hours at room temperature. It is poured onto 200 ml of water, and the resulting precipitate is filtered off with suction and washed with water. After drying, 2.3 g of a white powder remain.

Yield: 73.4%, m.p.: 174°–176° C.

Example 9

Methyl 3-N-acetylamino-3-phenyl-2-hydroxybutyrate 38.4 g (200 mmol) of methyl 3-phenyl-2,3-epoxybutyrate are dissolved in 400 ml of acetonitrile and treated with 56.8 g (400 mmol) of boron trifluoride etherate and the mixture is stirred for 4 hours at room temperature. After removing the solvent, the residual oil is taken up in 400 ml of methanol, treated with 100 g of silica gel and evaporated to dryness in a rotary evaporator. After washing with N-hexane/ethyl acetate 9:1, the mixture is extracted with methanol and the extract concentrated on a rotary evaporator. 31.6 g of a slightly yellow oil remain.

Yield: 62.9%

Example 10

Methyl 3-N-acetylamino-3-phenyl-2-(4,6-dimethoxypyrimidin-2-yl)oxybutyrate 12.5 g (50 mmol) of methyl 3-N-acetylamino-3-phenyl-2-hydroxybutyrate (Ex. 9) are dissolved in 80 ml of DMF. 3.4 g (25 mmol) of potassium carbonate and 10.8 g (50 mmol) of 4,6-dimethoxy-2-methylsulfonylpyrimidine are added and the mixture is stirred for 6 hours at 50° C. and for 12 hours at room temperature. The precipitate formed is filtered off with suction, washed with water and diethyl ether and dried. 9.7 g of a diastereomer are obtained as a white powder. After concentrating in the same manner, a further 5.5 g of diastereomer mixture are obtained from the mother liquor.

Yield: 78.1%, m.p.: 184°–185° C. (1 diastereomer)

Example 11

3N-acetylamino-3-phenyl-2-(4,6-dimethoxypyrimidin-2-yl)oxbutyrate 4.7 g (12 mmol) of methyl 3-N-acetylamino-3-phenyl-2-(4,6-dimethoxypyrimidin-2-yl)oxybutyrate (Ex. 10) are dissolved in 40 ml of methanol and 60 ml of THF, treated with 4.8 g (12 mmol) of 10% strength sodium hydroxide solution and stirred at room temperature for 2 days. The mixture is concentrated, and the residue is taken up in water and extracted with ethyl acetate. The aqueous phase is then adjusted to pH 2 using 10% strength hydrochloric acid and extracted with ethyl acetate. After drying and concentrating, 4.2 g of a white powder remain.

Yield: 92.5%, m.p.: 121° C. (decomposition)

Example 12

Methyl 3-azido-3-phenyl-2-[(4,6-dimethoxypyrimidin-2-yl)thio]butyrate 5.9 g (25 mmol) of methyl 3-azido-3-phenyl-2-hydroxybutyrate (Ex. 1) are dissolved in 50 ml of dichloromethane, 3 g (30 mmol) of triethylamine are added and 3.2 g (28 mmol) of methanesulfonyl chloride are added dropwise with stirring. The mixture is stirred for 23 hours at room temperature, washed three times with 100 ml of water each time, dried over sodium sulfate and concentrated under reduced pressure. The residue is taken up in 100 ml of DMF and added dropwise at 0° C. to a suspension of 12.9 g (75 mmol) of 4,6-dimethoxypyrimidine-2-thiol and 8.4 g (100 mmol) of sodium hydrogencarbonate in 100 ml of DMF. After stirring at room temperature for 2 hours and at 60° C. for a further 2 hours, the mixture is poured onto 1 l of ice water and the resulting precipitate is filtered off with suction.

All the compounds mentioned in Table 1 were prepared in a similar manner to the above examples.

TABLE 1

$$\underset{R^5}{\overset{R^4}{\text{(N)}-\underset{|}{\overset{|}{C}}-CH-COR^1}}$$

with Y—[pyrimidine with 4,6-di-OCH₃]

I where R = COR¹

| No. | (N) | R⁴ | R⁵ | R¹ | Y | Dia-stereomers | M.p. [°C.] |
|---|---|---|---|---|---|---|---|
| 1.1 | —N₃ | Phenyl | Methyl | OCH₃ | O | 1:0 | 118–120 |
| 1.2 | —N₃ | Phenyl | Methyl | OH | O | 1:0 | 193–195 |
| 1.3 | —N₃ | Phenyl | Methyl | OCH₃ | S | | |
| 1.4 | —N₃ | Phenyl | Methyl | OH | S | | |
| 1.5 | —N₃ | Methyl | Methyl | OCH₃ | O | — | 86-89 |
| 1.6 | —N₃ | Methyl | Methyl | OH | O | — | Oil |
| 1.7 | —N₃ | —(CH₂)₄— | | OCH₃ | O | — | 75–77 |
| 1.8 | —N₃ | —(CH₂)₄— | | OH | O | — | 110–112 |
| 1.9 | —N₃ | —(CH₂)₅— | | OCH₃ | O | — | 114 |
| 1.10 | —N₃ | —(CH₂)₅— | | OH | O | — | 138–140 |
| 1.11 | —NH—C₆H₅ | Phenyl | Methyl | OCH₃ | O | 3:2 | 131–139 |
| 1.12 | —NH—C₆H₅ | Phenyl | Methyl | OCH₃ | O | 1:0 | 174:176 |
| 1.13 | —NH—C₆H₅ | Phenyl | Methyl | ONa | O | 1:0 | 187(D) |
| 1.14 | —NH—C₆H₅ | Phenyl | Methyl | OH | O | 1:0 | 115 |
| 1.15 | —NH—(3-Cl-C₆H₄) | Phenyl | Methyl | OCH₃ | O | 1:1 | 115–125 |
| 1.16 | —NH—(3-Cl-C₆H₄) | Phenyl | Methyl | OH | O | 1:1 | 150(D) |
| 1.17 | —NH—C(O)—CH₃ | Phenyl | Methyl | OCH₃ | O | 5:4 | 150–154 |
| 1.18 | —NH—C(O)—CH₃ | Phenyl | Methyl | OCH₃ | O | 1:0 | 180–185 |
| 1.19 | —NH—C(O)—CH₃ | Phenyl | Methyl | OH | O | | |
| 1.20 | —NH—C(O)—CH₃ | Phenyl | Methyl | OH | O | 1:0 | 121(D) |
| 1.21 | —NH—C(O)—C₆H₅ | Phenyl | Methyl | OCH₃ | O | 1:0 | 85–90 |
| 1.22 | —NH—C(O)—C₆H₅ | Phenyl | Methyl | OH | O | | |
| 1.23 | —NH—C(O)—C₂H₅ | Phenyl | Methyl | OCH₃ | O | | |
| 1.24 | —NH—C(O)—C₂H₅ | Phenyl | Methyl | OH | O | | |
| 1.25 | N₃ | 2-Furyl | H | OCH₃ | O | 1:0 | Oil |
| 1.26 | N₃ | 2-Furyl | H | OH | O | 1:0 | Oil |
| 1.27 | N₃ | 3-Pyridyl | Methyl | OCH₃ | O | 1:0 | 121–124 |
| 1.28 | N₃ | 3-Pyridyl | Methyl | OH | O | 1:0 | 177 (Dec.) |
| 1.29 | —NH—CH₂—C₆H₅ | Phenyl | Methyl | NHCH₂C₆H₅ | O | 1:1 | 115 |

TABLE 1-continued

I where R = COR¹

Structure: (N)—C(R⁴)(R⁵)—CH(COR¹)— connected to pyrimidine ring with OCH₃ groups at positions and Y substituent.

| No. | (N) | R⁴ | R⁵ | R¹ | Y | Diastereomers | M.p. [°C.] |
|---|---|---|---|---|---|---|---|
| 1.30 | —NH—CH₂—C₆H₅ | Phenyl | Methyl | OH | O | | |
| 1.31 | —N(CH₃)—C(O)—CH₃ | Phenyl | Methyl | OCH₃ | O | | |
| 1.32 | —N(CH₃)—C(O)—CH₃ | Phenyl | Methyl | OH | O | | |
| 1.33 | —NH—C(O)—O—+ | Phenyl | Methyl | OCH₃ | O | | |
| 1.34 | —NH—C(O)—O—+ | Phenyl | Methyl | OH | O | | |
| 1.35 | —NH—C(O)—O—CH₂—C₆H₅ | Phenyl | Methyl | OCH₃ | O | | |
| 1.36 | —NH—C(O)—O—CH₂—C₆H₅ | Phenyl | Methyl | OH | O | | |
| 1.37 | —NH₂ | Phenyl | Methyl | OCH₃ | O | 1:0 | 75–79 |
| 1.38 | —NH₂ | Phenyl | Methyl | OH | O | | |
| 1.39 | —N(CH₃)₂ × HI | Phenyl | Methyl | OCH₃ | O | 1:0 | 116–118 |
| 1.40 | —N(CH₃)₂ | Phenyl | Methyl | OH | O | | |
| 1.41 | N₃ | 4-Chlorophenyl | Methyl | OCH₃ | O | 1:0 | 79–80 |
| 1.42 | N₃ | 4-Chlorophenyl | Methyl | OH | O | 1:0 | 180–183 |
| 1.43 | N₃ | 4-Bromophenyl | Methyl | OCH₃ | O | 1:0 | 85–87 |
| 1.44 | N₃ | 4-Bromophenyl | Methyl | OH | O | 1:0 | 153–155 |
| 1.45 | N₃ | 3-Nitrophenyl | Methyl | OCH₃ | O | | |
| 1.46 | N₃ | 3-Nitrophenyl | Methyl | OH | O | | |
| 1.47 | N₃ | 4-Trifluoromethylphenyl | Methyl | OCH₃ | O | | |
| 1.48 | N₃ | 4-Trifluoromethylphenyl | Methyl | OH | O | | |
| 1.49 | N₃ | 2-Fluorophenyl | Methyl | OCH₃ | O | 1:0 | 165–167 |
| 1.50 | N₃ | 2-Fluorophenyl | Methyl | OH | O | 1:0 | 155–157 |
| 1.51 | N₃ | 4-Fluorophenyl | Methyl | OCH₃ | O | 1:0 | 130–132 |
| 1.52 | N₃ | 4-Fluorophenyl | Methyl | OH | O | 1:0 | 185–186 |
| 1.53 | N₃ | 2-Methylphenyl | Methyl | OCH₃ | O | | |
| 1.54 | N₃ | 2-Methylphenyl | Methyl | OH | O | | |
| 1.55 | N₃ | 3-Methylphenyl | Methyl | OCH₃ | O | 1:0 | 68–70 |
| 1.56 | N₃ | 3-Methylphenyl | Methyl | OH | O | 1:0 | 125–126 |
| 1.57 | N₃ | 4-Methylphenyl | Methyl | OCH₃ | | | |
| 1.58 | N₃ | 4-Methylphenyl | Methyl | OH | O | | |
| 1.59 | N₃ | Phenyl | Ethyl | OCH₃ | O | 1:0 | 105–106 |
| 1.60 | N₃ | Phenyl | Ethyl | OH | O | 3:1 | Oil |
| 1.61 | —NH—C(O)—CH₃ | Methyl | Methyl | OCH₃ | O | | |
| 1.62 | —NH—C(O)—CH₃ | Methyl | Methyl | OH | O | | |
| 1.63 | —NH—C(O)—C₆H₅ | Methyl | Methyl | OCH₃ | O | | |

TABLE 1-continued $$\underset{R^5}{\overset{R^4}{\underset{|}{N}}}-\underset{|}{C}-CH-COR^1$$

with Y-pyrimidine ring bearing OCH₃ groups, I where R = COR¹

| No. | Ⓝ | R⁴ | R⁵ | R¹ | Y | Dia-stereo-mers | M.p. [°C.] |
|---|---|---|---|---|---|---|---|
| 1.64 | —NH—C(=O)—C₆H₅ | Methyl | Methyl | OH | O | | |
| 1.65 | N₃ | 3-Methoxy-phenyl | Methyl | OCH₃ | O | 1:0 | 125 |
| 1.66 | N₃ | 3-Methoxy-phenyl | Methyl | OH | O | 1:0 | 145–146 |
| 1.67 | N₃ | CH₃OCH₂— | Methyl | OCH₃ | O | | |
| 1.68 | N₃ | CH₃OCH₂— | Methyl | OH | O | 1:0 | Oil |
| 1.69 | —NH—C(=O)—CF₃ | Phenyl | Methyl | OCH₃ | O | | 129–130 |
| 1.70 | —NH—C(=O)—CF₃ | Phenyl | Methyl | OH | O | 1:0 | 91–95 |
| 1.71 | —NH—C(=O)—OCH₃ | Phenyl | Methyl | OCH₃ | O | 1:1 | Oil |
| 1.72 | —NH—C(=O)—OCH₃ | Phenyl | Methyl | OH | O | | |
| 1.73 | N₃ | Phenyl | Methyl | OCH₃ | O | 0:1 | 115–118 |
| 1.74 | N₃ | Phenyl | Methyl | OH | O | 0:1 | 171–173 |
| 1.75 | N₃ | 3-Thienyl | H | OCH₃ | O | 1:0 | 95–97 |
| 1.76 | N₃ | 3-Thienyl | H | OH | O | | |
| 1.77 | NH—C(=O)—O—C₆H₅ | Phenyl | Methyl | OCH₃ | O | 1:0 | 160–165 |
| 1.78 | NH—C(=O)—O—C₆H₅ | Phenyl | Methyl | OH | O | 1:0 | |

Use Examples

It was possible to show the herbicidal and growth-regulatory action of the lactic acid derivatives of the formula I by green-house tests:

The cultivation containers used were plastic pots containing loamy sand with about 3.0% of humus as a substrate. The seeds of the test plants were sown separately according to species.

In the case of pre-emergence treatment, the active compounds suspended or emulsified in water were applied directly after sowing by means of finely dispersing nozzles. The containers were lightly watered in order to promote germination and growth and then covered with transparent plastic hoods until the plants had taken root. This covering causes a uniform germination of the test plants if this has not been adversely affected by the active compounds. The application rate for pre-emergence treatment was 3.0 kg/ha of a.s.

For the purpose of post-emergence treatment, the test plants, depending on growth form, were first raised to a growth height of from 3 to 15 cm and only then treated with the active compounds suspended or emulsified in water. To do this, the test plants were either sown directly and raised in the same containers or they were first raised separately as seed plants and transplanted into the test containers a few days before the treatment. The application rate for post-emergence treatment was 3.0 kg/ha of a.s.

The plants were kept in a species-specific manner at 10°–25° C. or 20°–35° C. The test period extended over 2 to 4 weeks. During this time the plants were tended, and their reaction to the individual treatments was assessed.

The herbicidal action was assessed on a scale of from 0 to 100. 100 here means no emergence of the plants or complete destruction at least of the above-ground parts and 0 means no damage or normal course of growth.

The growth-regulating action was determined by height measurement. At the end of the test, the growth heights of the treated plants were measured and related to the growth heights of untreated plants.

The plants used in the greenhouse tests were made up of the following species

| Botanical Name | Common Name |
| --- | --- |
| Echinochloa crus-galli | barnyard grass |
| Galium aparine | cleavers |
| Ipomoea ssp. | morning glory |
| Lolium multiflorum | ital. ryegrass |
| Sinapis alba | white mustard |
| Setaria italica | millet foxtail |
| Brassica napus | rape |
| Triticum aestivum | wheat |
| Hordeum vulgare | barley |

The results showed a very good herbicidal action of compounds No. 1.2 and No. 1.6 according to the invention pre- and post-emergence.

Compound No. 1.14 further showed a very good growth-regulating action toward the crop plants spring barley, spring wheat and rape.

The effect of various representatives of the herbicidal composition combinations according to the invention, consisting of herbicide and compound having antidote action, on the growth of desired and undesired plants in comparison to the herbidical active compound on its own was confirmed in greenhouse tests:

In greenhouse tests the cultivation containers used were plastic pots having contents of around 300 cm³ and containing loamy sand with approximately 3.0% by weight of humus as a substrate. The seeds of the test plants were sown separately and evenly according to species and moistened. The containers were then covered with transparent plastic hoods until the seeds had germinated uniformly and the plants had taken root.

For post-emergence treatment, the test plants, depending on growth form, were first raised to a growth height of from 3 to 20 cm and only then treated. The herbicidal compositions were in this case suspended or emulsified in water as a dispersing agent and sprayed by means of finely dispersing nozzles.

Herbicides used as examples of the cyclohexenone derivatives XIII were

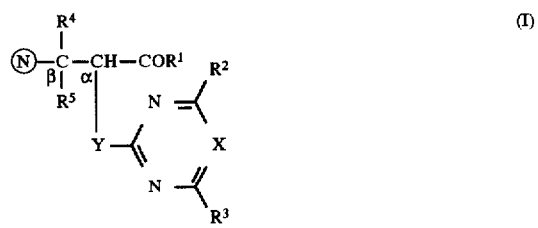

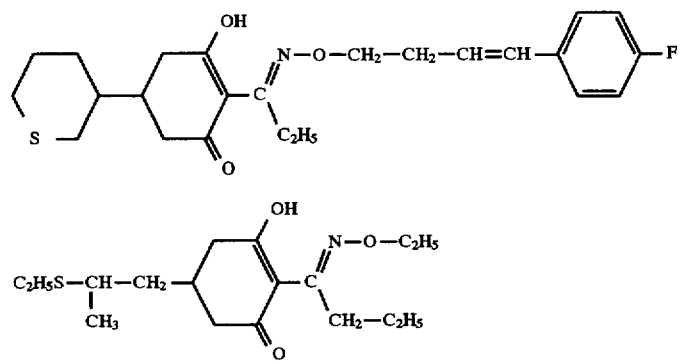

All compounds having antidote activity were prepared for post-emergence treatment in a mixture consisting of 80% by weight of cyclohexenone as diluent and 20% by weight of Emulphor® EL (ethoxylated castor oil) containing 10% by weight of active compound.

For comparison, the herbicidal active compound was formulated as a from 10 to 20% by weight emulsion concentrate and in each case introduced with addition of that amount of solvent system into the spray mixture using which the compound having antidote activity was applied at application rates indicated in the tables. The solution was prepared by mixing the active compound into a solution of 93% by weight of xylene and 7% by weight of Lutensol® AP-8 (nonionic surface-active agent based on alkylphenyl polyethylene glycol ethers).

After application of the respective active compound mixture, the test plants were cultivated in a greenhouse, to be specific heat-loving species at from approximately 18° to 30° C. and those from more temperate climates at from about 10° to 25° C.

The test period extended over from 3 to 5 weeks. During this time, the plants were tended, their reactions to the active compound treatments being determined.

The damage due to the chemical compositions was assessed with the aid of a scale from 0 to 100% in comparison to the untreated control plants. 0 in this case means no damage and 100 complete destruction of the plants.

By use of the lactic acid derivatives I, the tolerability of herbicidal cyclohexenone derivatives XIII by crop plants of the Gramineae family (grasses) such as wheat and corn was distinctly improved.

We claim:

1. A lactic acid, having an N-organic radical in the β-position, of the formula I $$\underset{R^5}{\overset{R^4}{\underset{|}{\text{(N)}-\underset{\beta}{C}-\underset{\alpha}{CH}-COR^1}}} \quad \underset{N-R^3}{\overset{R^2}{\underset{Y}{\overset{N}{\diagup}}\diagdown X}}$$

where the substituents have the following meanings:

$R^1$ is a radical $OR^9$, where $R^9$ is i) hydrogen, an alkali metal cation, the equivalent of an alkaline earth metal cation, the ammonium cation or an organic ammonium ion;

ii) a $C_3$–$C_8$-cycloalkyl group which can carry one to three $C_1$–$C_4$-alkyl radicals;

iii) a $C_1$–$C_8$-alkyl group which can carry one to five halogen atoms and one of the following radicals: $C_1$–$C_4$-alkoxy, $C_1$–$C_4$-alkylthio, cyano, $C_1$–$C_4$-alkylcarbonyl, $C_3$–$C_8$-cycloalkyl, $C_1$–$C_4$-alkoxycarbonyl, phenyl, or phenyl or phenoxy, which is mono- or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

iv) a $C_1$–$C_8$-alkyl group which can carry one to five halogen atoms and carries one of the following radicals: pyrazolyl, imidazolyl, benzimidazolyl, triazolyl, benzotriazolyl, isoxazolyl, oxazolyl and thiazolyl, bonded via a C atom or, if possible, N atom, where the heteroaromatic can carry one to four halogen atoms and one or two of the following radicals: nitro, cyano, $C_1$–$C_4$-alkyl, $C_1$–$C_4$- haloalkyl, $C_1$–$C_4$-alkoxy, phenyl, $C_1$–$C_4$-haloalkoxy and $C_1$–$C_4$-alkylthio;

v) a $C_2$–$C_6$-alkyl group which in the 2-position carries a radical selected from the group consisting of $C_1$–$C_4$-alkoxyimino, $C_3$–$C_6$-alkenyloxyimino, $C_3$–$C_6$-haloalkenyloxyimino and benzyloxyimino;

vi) a $C_3$–$C_6$-alkenyl or $C_3$–$C_6$-alkynyl group, where these groups for their part can carry one to five halogen atoms;

vii) a phenyl radical which can carry one to five halogen atoms and one to three of the following radicals: nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

Viii) a pyrazolyl, imidazolyl, benzimidazolyl, triazolyl, benzotriazolyl, preferably bonded via the 1-position, where the heteroaromatic can carry one or two of the radicals selected from the group consisting of halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and phenyl;

ix) a group

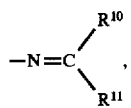

where
$R^{10}$ and $R^{11}$, which can be identical or different, are selected from the group consisting of $C_1$–$C_8$-alkyl, $C_3$–$C_6$-alkenyl, $C_3$–$C_6$-alkynyl, $C_3$–$C_8$-cycloalkyl, where these radicals can carry a $C_1$–$C_4$-alkoxy, $C_1$–$C_4$-alkylthio and a substituted or unsubstituted phenyl radical;

phenyl, which can be substituted by one or more of the radicals selected from the group consisting of halogen, nitro, cyano, $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio; or $R^{10}$ and $R^{11}$ together form a $C_3$–$C_{12}$-alkylene chain which can carry one to three $C_1$–$C_4$-alkyl groups and can contain a heteroatom from the group consisting of oxygen, sulfur and nitrogen;

$R^2$ is methoxy;

X is CH;

$R^3$ is methoxy;

$R^4$ is $C_1$–$C_8$-alkyl, which can carry one to five halogen atoms and one of the following radicals: $C_1$–$C_4$-alkoxy, $C_1$–$C_4$-alkylthio, cyano, hydroxyl, $C_1$–$C_4$-alkylcarbonyl, $C_1$–$C_4$-alkoxycarbonyl, phenyl, phenoxy and phenylcarbonyl;

$C_1$–$C_8$-alkyl, which can carry one to five halogen atoms and carries a pyrrolyl, pyrazolyl, imidazolyl, or triazolyl;

$C_3$–$C_8$-cycloalkyl or $C_3$–$C_8$-cycloalkenyl, where a methylene group in the saturated or unsaturated ring can be replaced by an oxygen or sulfur atom, where the cycloalkyl or cycloalkenyl radicals can be substituted by one to five halogen atoms and one of the following radicals: $C_1$–$C_4$-alkyl, $C_1$–$C_4$-alkoxy, $C_1$–$C_4$-alkylthio, cyano, $C_1$–$C_4$-alkylcarbonyl, $C_1$–$C_4$-alkoxycarbonyl and phenyl;

$C_3$–$C_6$-alkenyl or $C_3$–$C_6$-alkynyl, which can carry one to five halogen atoms and one of the following radicals: $C_1$–$C_4$-alkyl, $C_1$–$C_4$-alkoxy, $C_1$–$C_4$-alkylthio, cyano, $C_1$–$C_4$-alkylcarbonyl, $C_1$–$C_4$-alkoxycarbonyl and phenyl;

furyl, thienyl, pyrryl, pyrazolyl, imidazolyl, triazolyl, isoxazolyl, oxazolyl, isothiazolyl, thiazolyl, thiadiazolyl, pyridyl, pyrimidyl, pyrazinyl, pyridazinyl, triazinyl, oxa-2,4-diazolyl, oxa-3,4-diazolyl, where the heteroaryl rings can carry one to five halogen atoms and one of the following radicals: nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl, $C_1$–$C_4$-alkoxycarbonyl and phenyl;

phenyl or naphthyl, which can be substituted by one or more of the radicals selected from the group consisting of halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl and $C_1$–$C_4$-alkoxycarbonyl;

$R^5$ is hydrogen, $C_1$–$C_4$-alkyl, $C_3$–$C_6$-alkenyl, $C_3$–$C_6$-alkynyl, $C_1$–$C_4$-alkylcarbonyl, $C_3$–$C_8$-cycloalkyl, $C_1$–$C_4$-haloalkyl, $C_1$–$C_4$-alkoxyalkyl, $C_1$–$C_4$-alkoxycarbonyl, $C_1$–$C_4$-alkylthioalkyl or phenyl, or $R^4$ and $R^5$, together with the adjacent carbon atom, forms a 3- to 8-membered ring which can contain an oxygen or sulfur atom, and is unsubstituted or, depending on ring size, carries one to three of the radicals selected from the group consisting of $C_1$–$C_4$-alkyl, $C_1$–$C_4$-alkoxy, $C_1$–$C_4$-haloalkyl, $C_1$–$C_4$-haloalkoxy and $C_1$–$C_4$-alkylthio;

Y is sulfur or oxygen; and

Ⓝ is a radical $N_3$.

2. The lactic acid of the formula I as defined in claim 1, wherein $R^4$ is 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 5-thiazolyl, 2-imidazolyl, 4-imidazolyl, 5-imidazolyl, 2-pyrrolyl, 3-pyrrolyl, 4-pyrrolyl, 3-pyrazolyl, 4-pyrazolyl, 5-pyrazolyl, 2-pyridyl, 3-pyridyl, 4-pyridyl, oxa-2,4-diazolyl, oxa-3,4-diazolyl, thia-2,4-diazolyl, thia-3,4-diazolyl and triazolyl, where the heteroaryl rings can carry one to five halogen atoms and one of the following radicals: nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl, $C_1$–$C_4$-alkoxycarbonyl and phenyl.

3. The lactic acid of the formula I as defined in claim 1, wherein $R^4$ is 1-naphthyl, 2-naphthyl, 3-bromo-2-naphthyl, 4-methyl-1-naphthyl, 5-methoxy-1-naphthyl, 6-trifluoromethyl-1-naphthyl, 7-chloro-1-naphthyl or 8-hydroxy-1-naphthyl.

4. The lactic acid of the formula I as defined in claim 1, wherein $R^4$ is $C_1$–$C_8$-alkyl, which can carry one to five halogen atoms and carries a pyrrolyl, pyrazolyl, imidazolyl, or triazolyl, bonded via the N atom.

5. The lactic acid of the formula I as defined in claim 1, wherein $R^5$ is methyl.

6. A herbicidal composition containing a compound of the formula I as defined in claim 1 and customary inert additives.

7. A composition for regulating plant growth, containing a compound of the formula I as defined in claim 1 and customary inert additives.

8. A method of controlling undesired plant growth, which comprises allowing a herbicidally active amount of a compound of the formula I as defined in claim 1 to act on the plants or their habitat.

9. A method for regulating plant growth, which comprises allowing an active amount of a compound of the formula I as defined in claim 1 to act on the plants or their habitat.

* * * * *